United States Patent
Kamino et al.

(10) Patent No.: US 8,650,890 B2
(45) Date of Patent: Feb. 18, 2014

(54) HUMIDITY CONTROL SYSTEM

(75) Inventors: Akira Kamino, Osaka (JP); Nobuki Matsui, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 728 days.

(21) Appl. No.: 12/665,287

(22) PCT Filed: Jun. 10, 2008

(86) PCT No.: PCT/JP2008/001478
§ 371 (c)(1),
(2), (4) Date: Dec. 17, 2009

(87) PCT Pub. No.: WO2009/011086
PCT Pub. Date: Jan. 22, 2009

(65) Prior Publication Data
US 2010/0170281 A1    Jul. 8, 2010

(30) Foreign Application Priority Data

Jul. 19, 2007 (JP) ................................. 2007-188377

(51) Int. Cl.
*F24F 3/16* (2006.01)
*F25D 17/06* (2006.01)

(52) U.S. Cl.
USPC ................... 62/78; 62/303; 62/92; 62/271

(58) Field of Classification Search
USPC ...................... 62/303, 78, 92, 271
See application file for complete search history.

(56) References Cited

U.S. PATENT DOCUMENTS

| | | | |
|---|---|---|---|
| 2004/0262241 A1 | 12/2004 | Socha | |
| 2006/0207429 A1 | 9/2006 | Yabu | |
| 2006/0218943 A1 * | 10/2006 | Yabu et al. | 62/94 |
| 2007/0039343 A1 * | 2/2007 | Ikegami et al. | 62/271 |
| 2009/0118870 A1 | 5/2009 | Matsui | |
| 2009/0134231 A1 | 5/2009 | Matsui | |

FOREIGN PATENT DOCUMENTS

| | | |
|---|---|---|
| CN | 1836135 A | 9/2006 |
| GB | 2-253-478 A | 9/1992 |
| JP | 2000-051643 A | 2/2000 |
| JP | 2001-178803 A | 7/2001 |
| JP | 2002-343535 A | 11/2002 |
| JP | 2003-236332 A | 8/2003 |
| JP | 2005-098621 A | 4/2005 |
| JP | 2006-38449 A | 2/2006 |
| JP | 2006038449 A * | 2/2006 |
| JP | 2006-78108 A | 3/2006 |
| JP | 2006-329596 A | 12/2006 |
| WO | WO 2006/126543 A1 | 11/2006 |
| WO | WO 2006/126605 A1 | 11/2006 |

OTHER PUBLICATIONS

Database WPI Week 200375 dated Aug. 26, 2003, Thomson Scientific, London, GB; AN 2003-793795 (JP-2003-236332-A), XP002594602.

Database WPI Week 200613 dated Feb. 9, 2006, Thomson Scientific, London, GB; AN 2006-123228 (JP-2006-38449-A), XP0028594601.

* cited by examiner

*Primary Examiner* — Ljiljana Ciric
*Assistant Examiner* — Alexis Cox

(57) ABSTRACT

A closed space forming unit (41-48) forms a closed space (37, 38) around an adsorption member (51, 52) supporting thereon an adsorbent for desorbing and adsorbing moisture. An active species generating unit (101, 102) supplies active species, for decomposing odorous components, into the closed space (37, 38).

3 Claims, 14 Drawing Sheets

FIG. 13
(A)
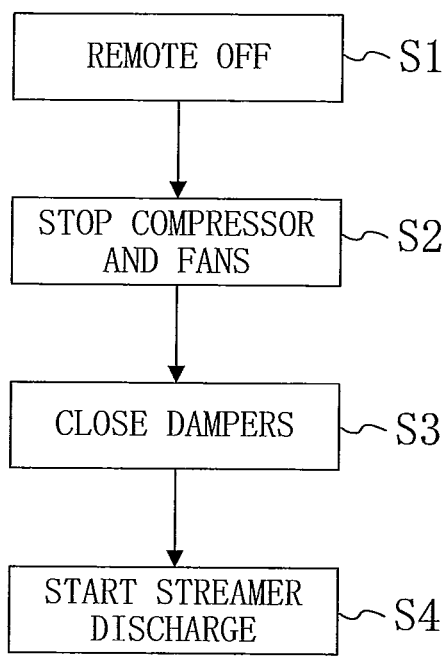
(B)
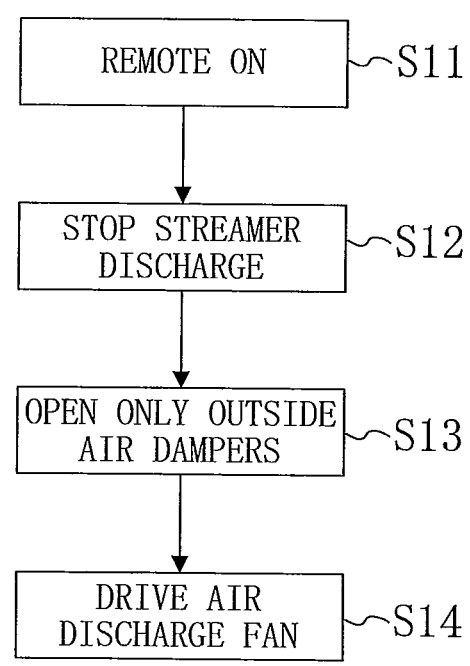

HUMIDITY CONTROL SYSTEM

TECHNICAL FIELD

The present invention relates to humidity control systems for controlling the humidity in a room by using an adsorbent for adsorbing and desorbing moisture.

BACKGROUND ART

Conventionally, humidity control systems for controlling the humidity of air by using an adsorbent are known in the art. Patent Document 1 discloses a humidity control system having adsorption heat exchangers having an adsorbent supported on their surfaces.

The humidity control system disclosed in Patent Document 1 is provided with a refrigerant circuit having two adsorption heat exchangers. This refrigerant circuit alternately performs two operations: an operation in which a first adsorption heat exchanger serves as a condenser, and a second adsorption heat exchanger serves as an evaporator; and an operation in which the second adsorption heat exchanger serves as a condenser, and the first adsorption heat exchanger serves as an evaporator. In the adsorption heat exchanger operating as an evaporator, moisture in the air is adsorbed by the adsorbent. In the adsorption heat exchanger operating as a condenser, moisture is desorbed from the adsorbent into the air.

The humidity control system disclosed in Patent Document 1 supplies one of air streams that have respectively passed through the adsorption heat exchangers, into the room, and discharges the other air stream out of the room. For example, when the humidity control system is in a dehumidification mode, air flow paths in a casing are determined so that an air stream, which has passed through one of the first and second adsorption heat exchangers operating as an evaporator, is supplied into the room, and an air stream, which has passed through the other adsorption heat exchanger operating as a condenser, is discharged out of the room (see FIGS. 4 and 5 of Patent Document 1).

The humidity control system disclosed in Patent Document 1 also ventilates the room. For example, when in the dehumidification mode, the humidity control system supplies intake outside air into the room after dehumidifying the air in the adsorption heat exchanger operating as an evaporator, and, at the same time, discharges intake room air out of the room, together with moisture desorbed from the adsorption heat exchanger operating as a condenser.

PATENT DOCUMENT

PATENT DOCUMENT 1: Japanese Published Patent Application No. 2006-078108

SUMMARY OF THE INVENTION

Technical Problem

Incidentally, in this type of humidity control system, intake air continuously passes through the adsorption heat exchangers. Thus, odorous components (e.g., ammonia, a tobacco odor, and the like) contained in the air can be adsorbed by the adsorbent. Moreover, a musty odor and the like can be adsorbed by the adsorbent if mold and bacteria grow around the adsorption heat exchangers. If such odorous components are adsorbed by the adsorbent, concentrated odorous components can be desorbed into the air during the subsequent humidity control operation. As a result, the air containing the odorous components is supplied into the room, making the room uncomfortable.

The present invention was developed in view of the above problem, and it is an object of the present invention to prevent odorous components, adsorbed in an adsorbent, from being supplied into a room in a humidity control system for controlling the humidity of air by the adsorbent.

Solution to the Problem

According to a first invention, a humidity control system includes: a casing (11) having air passages formed therein; an adsorption member (51, 52), which is provided in the air passages of the casing (11), and supports thereon an adsorbent capable of adsorbing moisture in air and desorbing moisture into the air, where the humidity control system controls humidity of air by the adsorption member (51, 52), and supplies the resultant air into a room. The humidity control system further includes: a closed space forming unit (41-48) for forming a closed space (37, 38) around the adsorbent member (51, 52) so as to hermetically seal the adsorbent member (51, 52) therein; and an active species generating unit (101, 102) for supplying active species, for decomposing odorous components, into the closed spaces (37, 38).

In the first invention, the adsorption member (51, 52) is disposed in the air passages of the casing (11). The adsorbent capable of desorbing and adsorbing moisture is supported on the adsorption member (51, 52). Air is dehumidified when, e.g., moisture in the air is adsorbed by the adsorbent while the air is passing through the adsorption member (51, 52). Air is humidified when, e.g., moisture in the adsorbent is desorbed into the air while the air is passing through the adsorption member (51, 52). The humidity control system controls the humidity in a room by supplying such dehumidified or humidified air into the room.

Incidentally, odorous components can be adsorbed by the adsorbent of the adsorption member (51, 52), as described above. Thus, the humidity control system of the present invention is provided with the closed space forming unit (41-48) and the active species generating unit (101, 102) in order to decompose the odorous components adsorbed in the adsorption member (51, 52). Specifically, the closed space forming unit (41-48) forms the closed space (37, 38) around the adsorption member (51, 52) so as to hermetically seal the adsorption member (51, 52) therein. Thus, the adsorption member (51, 52) is disconnected from the outside of the casing (11). The active species generating unit (101, 102) supplies active species into the closed space (37, 38) formed as described above. Examples of the active species include fast electrons, ions, ozone, radicals such as hydroxy radicals, and other excited molecules (such as excited oxygen molecules, excited nitrogen molecules, and excited water molecules).

When the active species is supplied into the closed space (37, 38) that hermetically seals the adsorption member (51, 52) therein, the active species react with the odorous components adsorbed by the adsorbent. As a result, the odorous components are decomposed. Since the adsorption member (51, 52) is located in the closed space (37, 38), the active species, which is supplied to the closed space (37, 38), can be maintained at a high concentration. This facilitates the reaction between the active species and the odorous components, whereby the odorous components are reliably decomposed.

According to a second invention, in the humidity control system of the first invention, a plurality of open/close dampers (41-48) are provided in the casing (11), where the open/ close dampers (41-48) are capable of switching air flow paths by connecting and disconnecting the air passages, located on inlet and outlet sides of the absorption member (51, 52), to and from each other, and the closed space forming unit (41-48) is formed by the plurality of open/close dampers (41-48), where the open/close dampers (41-48) form the closed space (37, 38) around the adsorption member (51, 52) when closed.

In the second invention, the plurality of open/close dampers (41-48) are provided in the air passages in the casing (11). The open/close dampers (41-48) are positioned on the inlet and outlet sides of the adsorption member (51, 52). The air passages on the inlet and outlet sides of the adsorption member (51, 52) are connected to, and disconnected from each other according to the open/closed state of the open/close dampers (41-48), whereby the air flow paths are switched as appropriate.

In the present invention, the open/close dampers (41-48) are used as the closed space forming unit (41-48). That is, the closed space (37, 38) is formed around the adsorption member (51, 52) by closing the open/close dampers (41-48). By supplying the active species into the closed space (37, 38), the odorous components adsorbed in the adsorbent of the adsorption member (51, 52) are decomposed.

According to a third invention, the humidity control system of the first or second invention performs an operation of discharging air in the closed space (37, 38) out of the room, after the active species generating unit (101, 102) finishes its operation of supplying the active species into the closed space (37, 38).

In the third invention, the operation of discharging the air in the closed space (37, 38) out of the room is performed after the operation of supplying the active species into the closed space (37, 38) is finished. That is, although unreacted active species can remain in the closed space (37, 38) after decomposing the odorous components adsorbed by the adsorbent, such unreacted active species are discharged out of the room together with the air, according to the present invention. This reliably prevents the remaining active species from remaining in the casing (11), and from being supplied into the room afterwards.

According to a fourth invention, in the humidity control system of any one of the first to third inventions, the active species generating unit is formed by a streamer discharge apparatus (101, 102) for generating the active species by a streamer discharge.

In the fourth invention, the streamer discharge apparatus is used as the active species generating unit. In the streamer discharge, a high concentration of active species can be generated by generation of a low temperature plasma. Thus, the odorous components adsorbed in the adsorbent can be very efficiently decomposed by the active species. Moreover, the streamer discharge apparatus produces a so-called ionic wind when generating the streamer discharge. This ionic wind can produce an air current in the closed space (37, 38). This increases the efficiency of contact between the active species and the odorous components, thereby further increasing the efficiency of decomposition of the odorous components.

Advantages of the Invention

The closed space forming unit (41-48) for forming the closed space (37, 38) around the adsorption member (51, 52), and the active species generating unit (101, 102) for supplying the active species into the closed space (37, 38) are provided in the present invention. Thus, according to the present invention, the odorous components adsorbed by the adsorbent of the adsorption member (51, 52) can be decomposed by the active species, whereby concentration of the odorous components in the adsorbent can be prevented. This can prevent the concentrated odorous components from being desorbed from the adsorbent and supplied into the room when the humidity control system is in the mode of controlling the humidity in the room (the humidity control mode), thereby making it possible to keep the room sufficiently comfortable.

In the present invention, the adsorption member (51, 52) is located in the closed space (37, 38). This can increase the concentration of the active species in the closed space (37, 38), and thus, can increase the efficiency of decomposition of the odorous components. Moreover, since the adsorption member (51, 52) is located in the closed space (37, 38), leakage of the remaining active species into the room and the like can be prevented.

Moreover, in the present invention, the active species can prevent bacteria and mold from growing near the adsorption member (51, 52). This enables clean air to be supplied into the room during the humidity control mode. This can also prevent reduction in adsorption/desorption capability of the adsorbent, which is caused by the mold and the like growing on the surface of the adsorbent.

In particular, in the second invention, the open/close dampers (41-48) for switching the air flow paths are used to form the closed space (37, 38) around the adsorption member (51, 52). Thus, according to the present invention, the closed space (37, 38) can be formed by the minimum required number of parts, and the above functions and effects can be obtained.

In the third invention, the operation of discharging the air in the closed space (37, 38) out of the room is performed after the operation of supplying the active species into the closed space (37, 38) is finished. Thus, according to the present invention, the active species remaining in the closed space (37, 38) can be discharged out of the room, and the active species can be reliably prevented from being supplied into the room in the subsequent operation.

In the fourth invention, the active species are generated by the streamer discharge apparatus (101, 102). Thus, according to the present invention, a high concentration of active species can be supplied into the closed space (37, 38), and the efficiency of contact between the active species and the odorous components can be increased by the ionic wind. This enables the odorous components adsorbed by the adsorbent to be more reliably decomposed, thereby making the room more comfortable.

BRIEF DESCRIPTION OF THE DRAWINGS

FIG. 6(A) illustrates an operation during a first operation, and FIG. 6(B) illustrates an operation during a second operation.

FIG. 13(A) schematically illustrates a control flow when the humidity control system is stopped, and FIG. 13(B) schematically illustrates a control flow right after the humidity control system is started.

DESCRIPTION OF REFERENCE CHARACTERS

Figure 1:
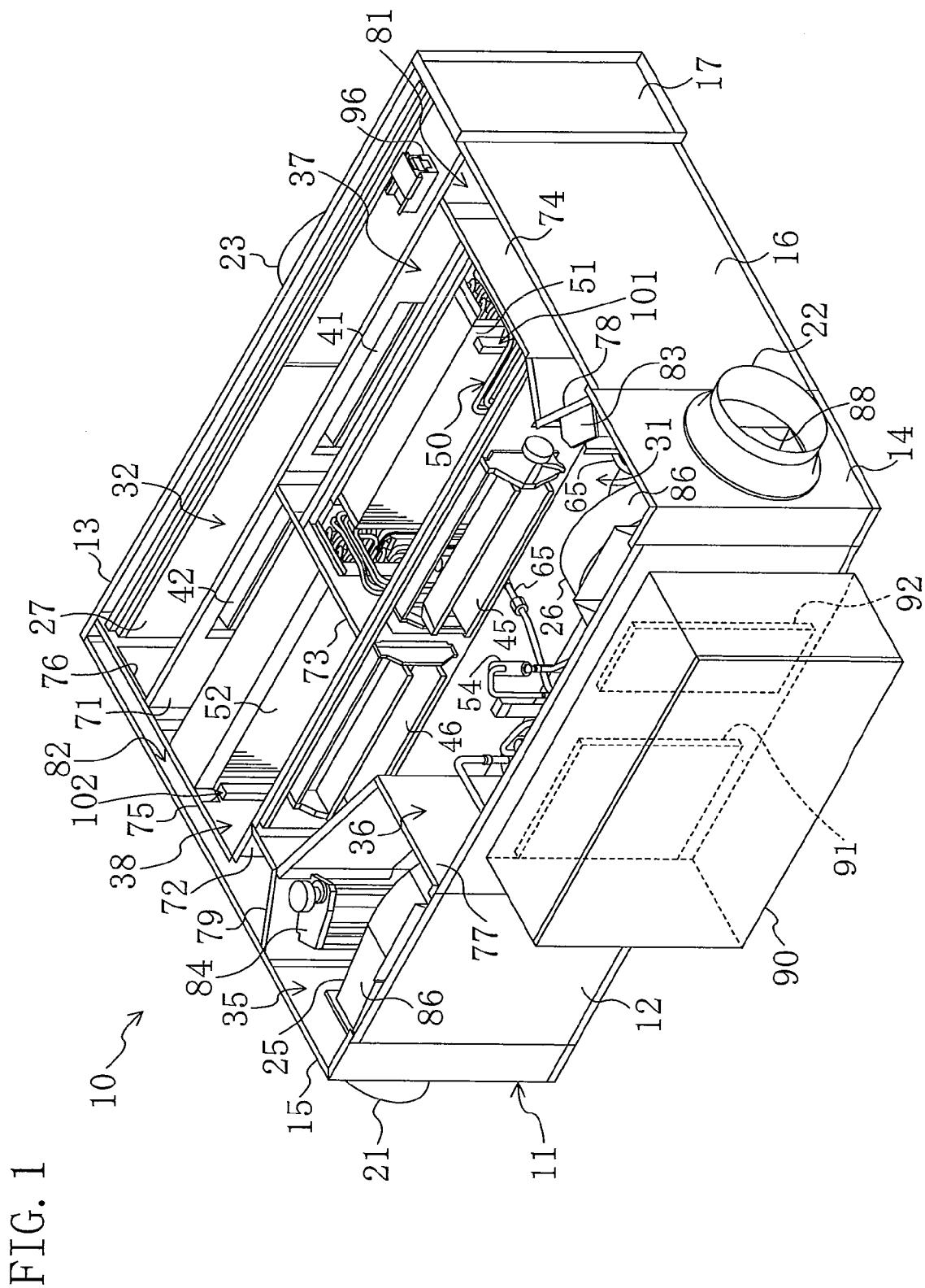
FIG. 1 is a perspective view of a humidity control system when viewed from its front side, where a top plate of a casing is omitted.

10 Humidity Control System
11 Casing
37 First Heat Exchanger Chamber (a Closed Space)
38 Second Heat Exchanger Chamber (a Closed Space)
41 First Room Air Damper (an Open/Close Damper, a Closed Space Forming Unit)
42 Second Room Air Damper (an Open/Close Damper, a Closed Space Forming Unit)
43 First Outside Air Damper (an Open/Close Damper, a Closed Space Forming Unit)
44 Second Outside Air Damper (an Open/Close Damper, a Closed Space Forming Unit)
45 First Supply Air Damper (an Open/Close Damper, a Closed Space Forming Unit)
46 Second Supply Air Damper (an Open/Close Damper, a Closed Space Forming Unit)
47 First Discharge Air Damper (an Open/Close Damper, a Closed Space Forming Unit)
48 Second Discharge Air Damper (an Open/Close Damper, a Closed Space Forming Unit)
51 First Adsorption Heat Exchanger (an Adsorption Member)
52 Second Adsorption Heat Exchanger (an Adsorption Member)
101 First Discharge Unit (a Streamer Discharge Apparatus, an Active Species Generating Unit)
102 Second Discharge Unit (a Streamer Discharge Apparatus, an Active Species Generating Unit)

DESCRIPTION OF EMBODIMENTS

An embodiment of the present invention will be described in detail below with reference to the accompanying drawings. A humidity control system (10) of the present embodiment is a system for controlling the humidity in a room and ventilating the room. The humidity control system (10) controls the humidity of intake outside air (OA) to supply the resultant air into the room, and, at the same time, discharges intake room air (RA) out of the room.

[Overall Configuration of the Humidity Control System]

The humidity control system (10) will be described below with reference to FIGS. 1 through 5. Note that the terms "upper," "lower," "left," "right," "front," and "rear" as used herein refer to the directions when the humidity control system (10) is viewed from its front side, unless otherwise specified.

The humidity control system (10) includes a casing (11). A refrigerant circuit (50) is accommodated in the casing (11). A first adsorption heat exchanger (51), a second adsorption heat exchanger (52), a compressor (53), a four-way selector valve (54), and an electric expansion valve (55) are connected to the refrigerant circuit (50). The refrigerant circuit (50) will be described in detail later.

The casing (11) has a somewhat flat rectangular parallelepiped shape having a relatively low height. The lateral width of the casing (11) is somewhat larger than the depth (the longitudinal width) thereof (see FIG. 3). A part of the casing (11), which forms a left front side face in FIG. 1 (i.e., a front face), is a front panel portion (12), and a part of the casing (11), which forms a right rear face in FIG. 1 (i.e., a rear face), is a rear panel portion (13). A part of the casing (11), which forms a right front side face in FIG. 1, is a first side panel portion (14), and a part of the casing (11), which forms a left rear side face in FIG. 1, is a second side panel portion (15).

In the casing (11), the front panel portion (12) and the rear panel portion (13) face each other, and the first side panel portion (14) and the second side panel portion (15) face each other. The first side panel portion (14) and the second side panel portion (15) form a side plate portion in the casing (11).

An outside air intake port (24), a room air intake port (23), an air supply port (22), and an air discharge port (21) are formed in the casing (11).

Figure 3:
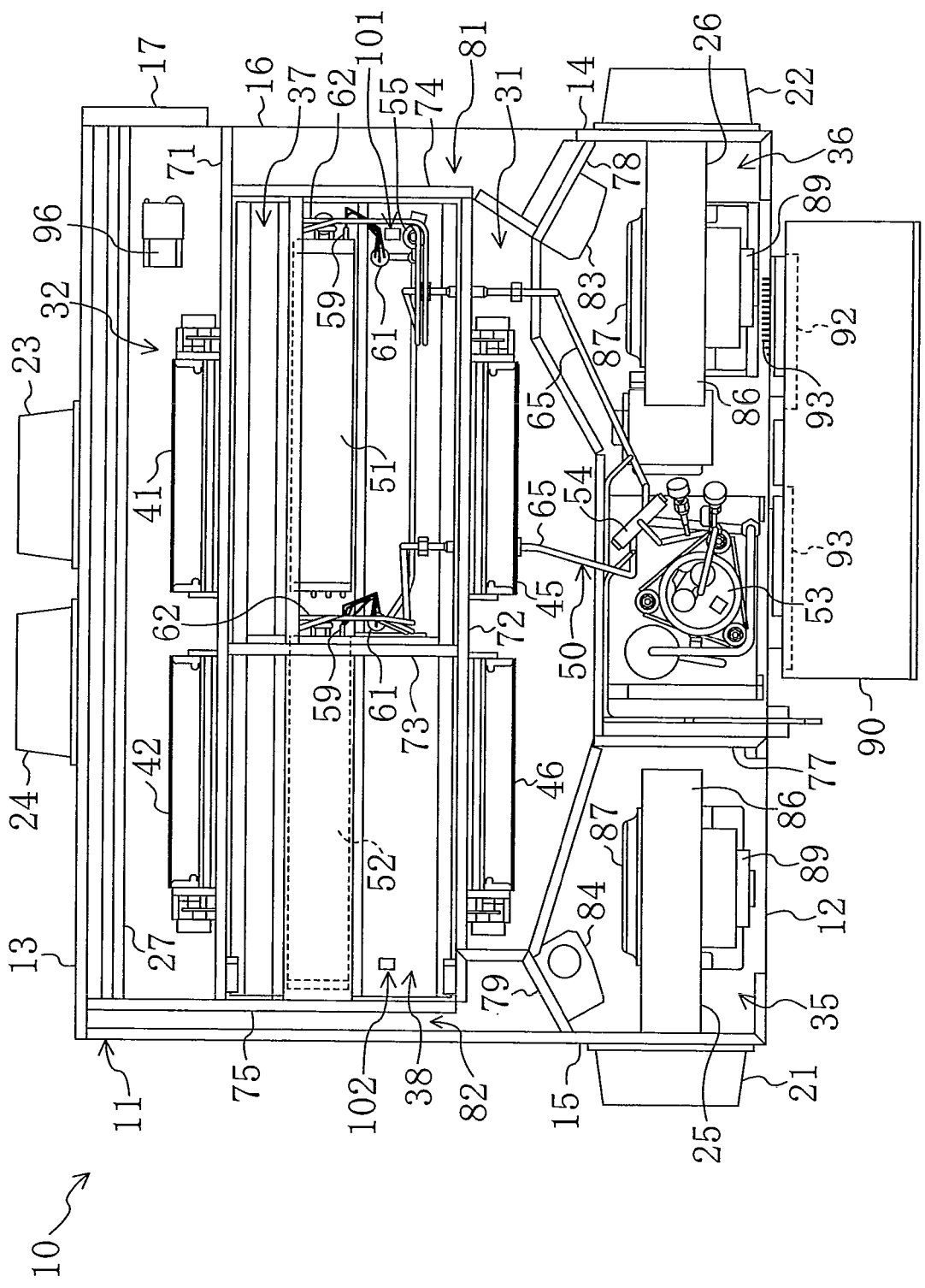
FIG. 3 is a plan view of the humidity control system, where the top plate of the casing is omitted.
Figure 4:
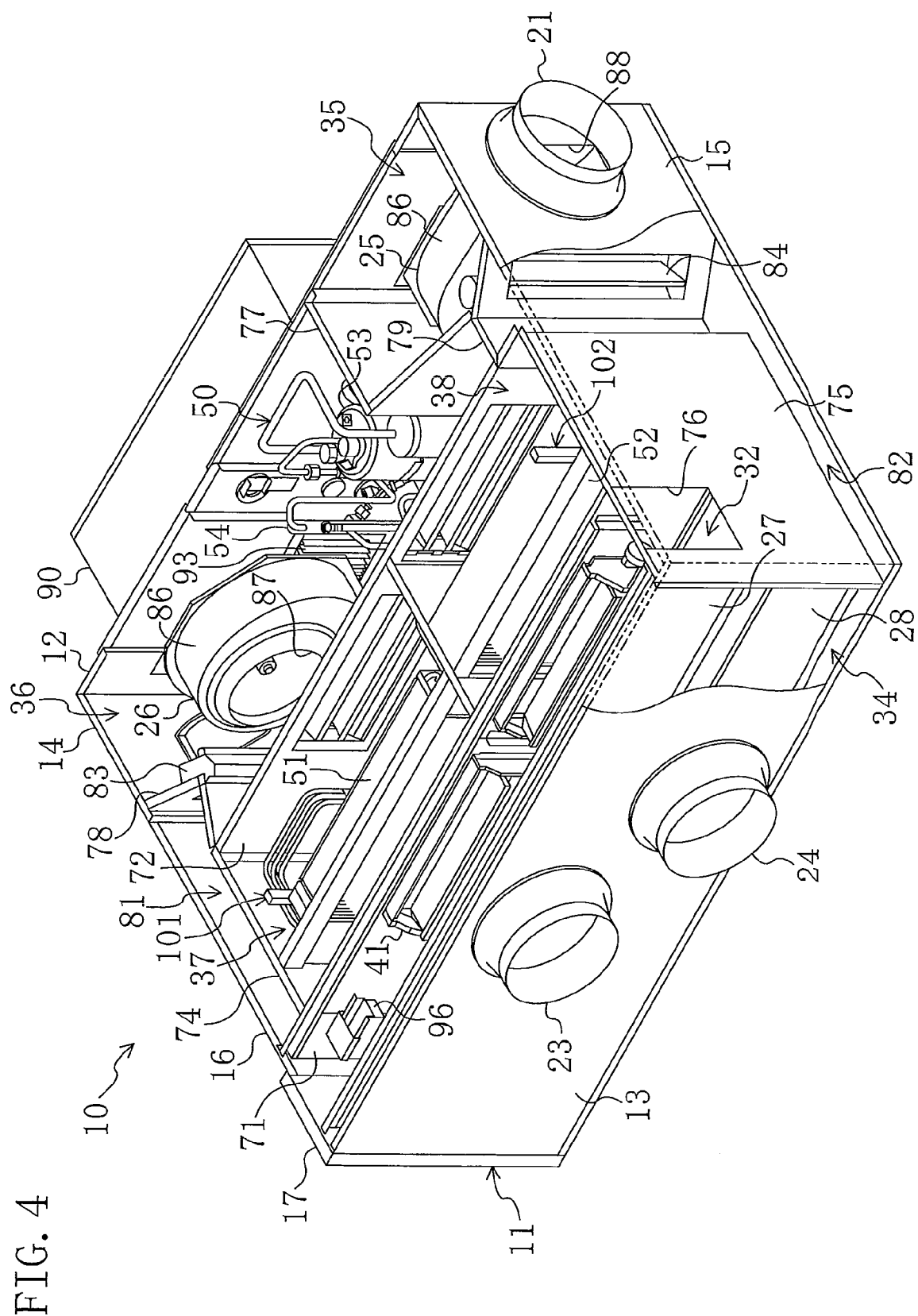
FIG. 4 is a perspective view of the humidity control system when viewed from its back side, where the top plate of the casing is omitted.

The outside air intake port (24) and the room air intake port (23) are formed in the rear panel portion (13) (see FIGS. 3 and 4). The outside air intake port (24) is positioned in a lower part of the rear panel portion (13). The outside air intake port (24) is disposed at a position that is offset from the center in the lateral direction of the rear panel portion (13) toward the second side panel portion (15). The indoor air intake port (23) is positioned in an upper part of the rear panel portion (13). The indoor air intake port (23) is disposed at a position that is offset from the center in the lateral direction of the rear panel portion (13) toward the first side panel portion (14).

The air supply port (22) is positioned near an end of the first side panel portion (14), which is located on the front panel portion (12) side. The air discharge port (21) is positioned near an end of the second side panel portion (15), which is located on the front panel portion (12) side.

An upstream partition plate (71), a downstream partition plate (72), a central partition plate (73), a first partition plate (74), and a second partition plate (75) are provided in the internal space of the casing (11). These partition plates (71-75) stand vertically on a bottom plate of the casing (11), and divide the internal space of the casing (11) along the entire height from the bottom plate of the casing (11) to a top plate thereof.

The upstream partition plate (71) and the downstream partition plate (72) are positioned parallel to the front panel portion (12) and the rear panel portion (13). In the internal space of the casing (11), the upstream partition plate (71) is positioned closer to the rear panel portion (13), and the downstream partition plate (72) is positioned closer to the front panel portion (12).

The lateral width of the upstream partition plate (71) is smaller than that of the casing (11). A right end of the upstream partition plate (71) is bonded with the first side panel portion (14). On the other hand, a gap is formed between a left end of the upstream partition plate (71) and the second side panel portion (15).

The lateral width of the downstream partition plate (72) is smaller than that of the upstream partition plate (71). A gap is formed between a right end of the downstream partition plate (72) and the first side panel portion (14). A gap is also formed between a left end of the downstream partition plate (72) and the second side panel portion (15).

The first partition plate (74) is positioned so as to close the space between the upstream partition plate (71) and the downstream partition wall (72) from the right side. Specifically, the first partition plate (74) is positioned parallel to the first side panel portion (14), and perpendicular to the upstream partition plate (71) and the downstream partition plate (72). A front end of the first partition plate (74) is bonded with the right end of the downstream partition plate (72). A rear end of the first partition plate (74) is bonded with the downstream partition plate (72).

The second partition plate (75) is positioned so as to close the space between the upstream partition plate (71) and the downstream partition wall (72) from the left side. Specifically, the second partition plate (75) is positioned parallel to the second side panel portion (15), and perpendicular to the upstream partition plate (71) and the downstream partition plate (72). A front end of the second partition plate (75) is bonded with the left end of the downstream partition plate (72). A rear end of the second partition plate (75) is bonded with the rear panel portion (13). The left end of the upstream partition plate (71) is bonded with the second partition plate (75).

The central partition plate (73) is positioned between the upstream partition plate (71) and the downstream partition plate (72) so as to be perpendicular to the upstream partition plate (71) and the downstream partition plate (72). The central partition plate (73) extends from the upstream partition plate (71) to the downstream partition plate (72), and divides the space between the upstream partition plate (71) and the downstream partition plate (72) into right and left spaces. The central partition plate (73) is disposed at a position that is somewhat offset from the respective centers in the lateral direction of the upstream partition plate (71) and the downstream partition plate (72) toward the second side panel portion (15).

Figure 2:
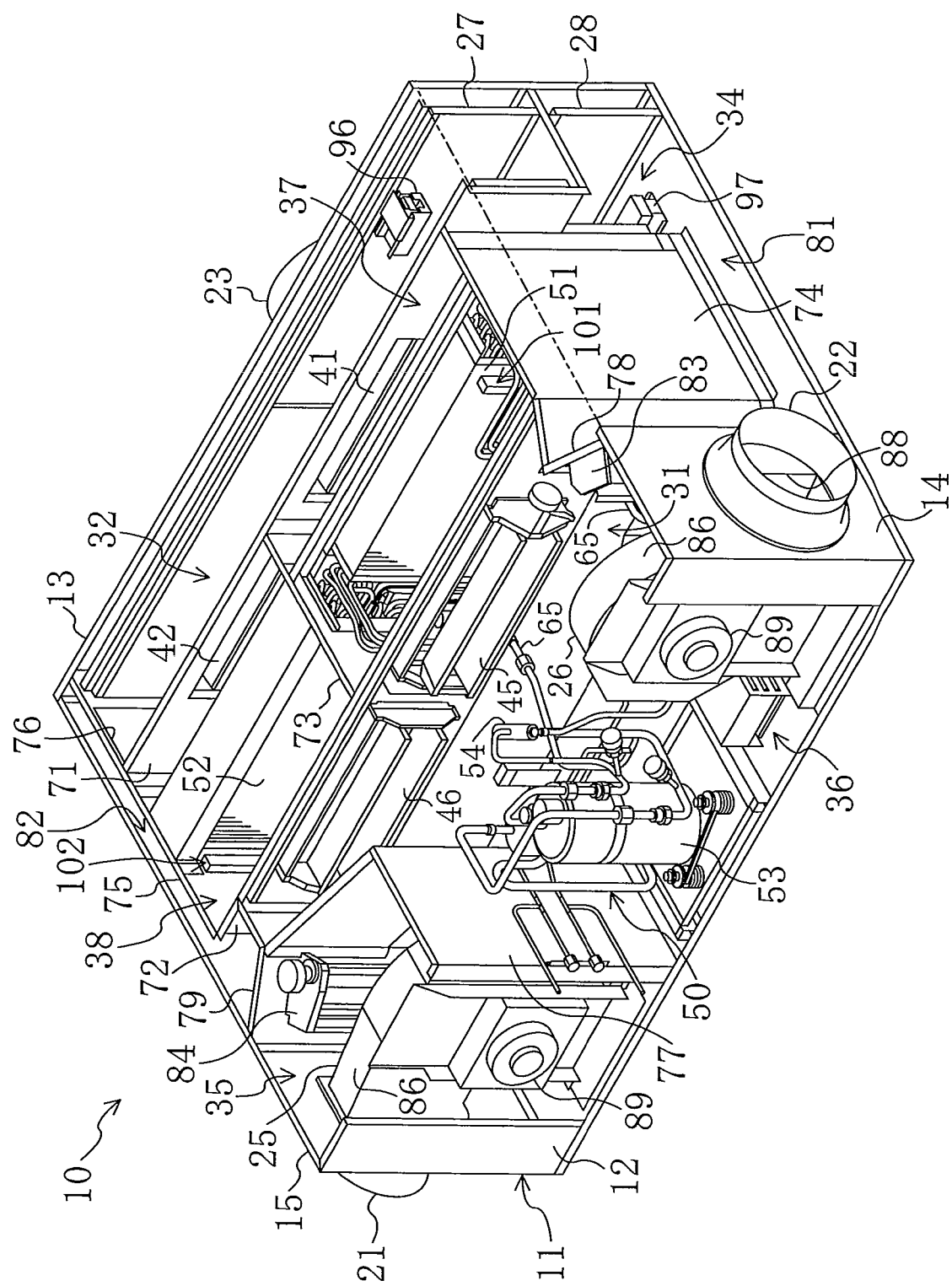
FIG. 2 is a perspective view of the humidity control system when viewed from its front side, where a part of the casing, and an electrical equipment box are omitted.
Figure 5:
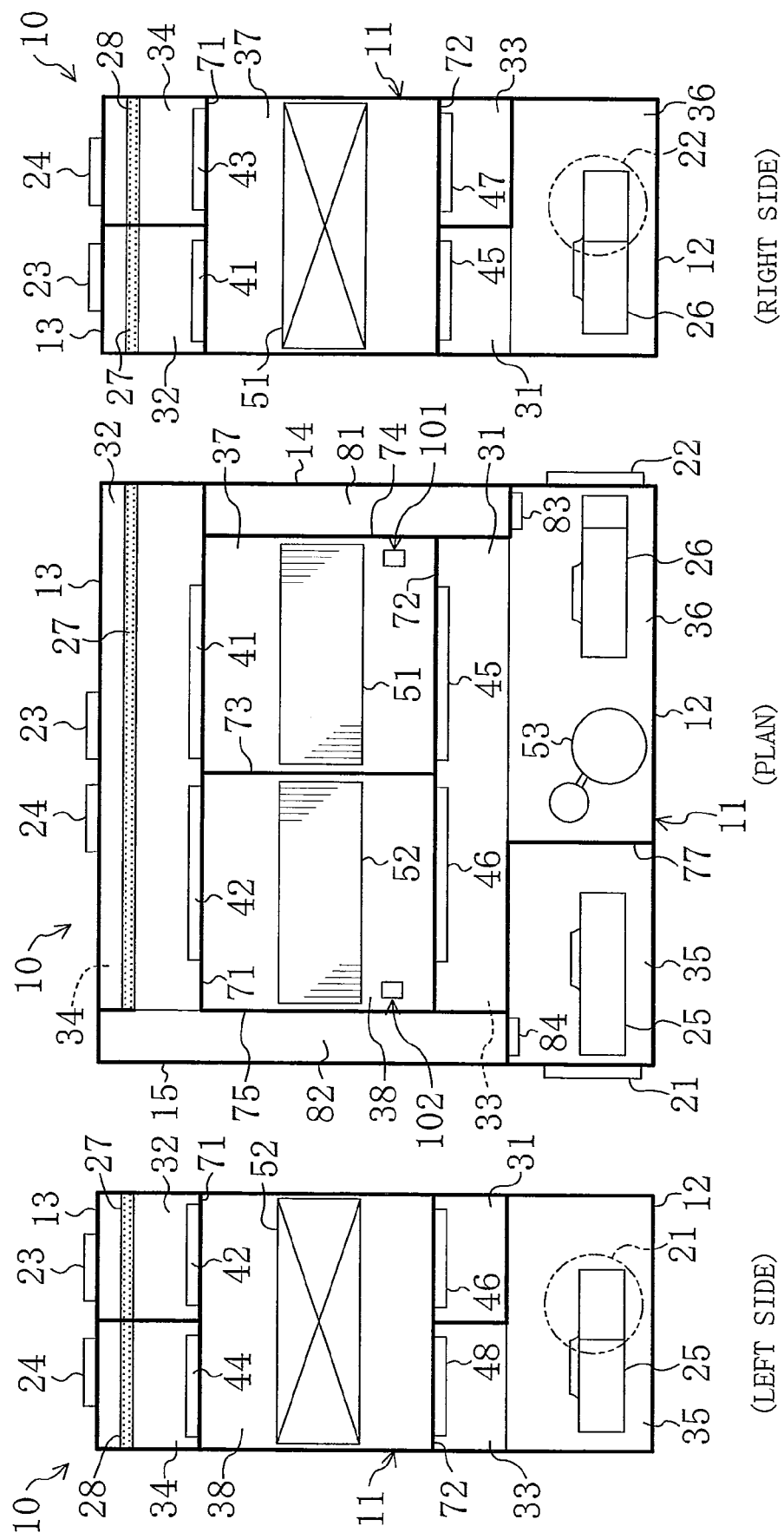
FIG. 5 shows a schematic plan view, and schematic right and left side views of the hydraulic control system, where a part of the hydraulic control system is omitted.

In the casing (11), the space between the upstream partition plate (71) and the rear panel portion (13) is divided into two (upper and lower) spaces (see FIGS. 2, 4, and 5). Of these two spaces, the upper space forms a room air passage (32), and the lower space forms an outside air passage (34).

The room air passage (32) communicates with a room via a duct connected to the room air intake port (23). A room air filter (27) for removing dust and the like from air is provided in the room air passage (32). The room air filter (27) has a rectangular plate shape whose longer side extends in the lateral direction, and the room air filter (27) stands in the room air passage (32) so as to extend laterally across the room air passage (32). The room air passage (32) is divided into front and rear passages by the room air filter (27). A room air humidity sensor (96) is accommodated in a part of the room air passage (32), which is located forward (downstream) of the room air filter (27). The room air humidity sensor (96) is attached to the top plate of the casing (11), and measures the relative humidity of air.

The outside air passage (34) communicates with the outside space via a duct connected to the outside air intake port (24). An outside air filter (28) for removing dust and the like from air is provided in the outside air passage (34). The outside air filter (28) has a rectangular plate shape whose longer side extends in the lateral direction, and the outside air filter (28) stands in the outside air passage (34) so as to extend laterally across the outside air passage (34). The outside air passage (34) is divided into front and rear passages by the outside air filter (28). An outside air humidity sensor (97) is accommodated in a part of the outside air passage (34), which is located forward (downstream) of the outside air filter (28). The outside air humidity sensor (97) is attached to the bottom plate of the casing (11), and measures the relative humidity of air.

As described above, the space between the upstream partition plate (71) and the downstream partition plate (72) in the casing (11) is divided into right and left spaces by the central partition plate (73). Of these spaces, the right space (the space on the right side of the central partition plate (73)) forms a first heat exchanger chamber (37), and the left space (the space on the left side of the central partition plate (73)) forms a second heat exchanger chamber (38) (see FIGS. 1 and 3).

The first adsorption heat exchanger (51) is accommodated in the first heat exchanger chamber (37), and the second adsorption heat exchanger (52) is accommodated in the second heat exchanger chamber (38). The overall shape of each adsorption heat exchanger (51, 52) is a rectangular thick plate shape, or a flat rectangular parallelepiped shape. The adsorption heat exchangers (51, 52) will be described in detail later.

A first discharge unit (101) is accommodated in the first heat exchanger chamber (37), and a second discharge unit (102) is accommodated in the second heat exchanger chamber (38). The first discharge unit (101) is positioned closer to the first partition plate (74), and in front of the first adsorption heat exchanger (51) in the first heat exchanger chamber (37). That is, the first discharge unit (101) is positioned on the air outlet side of the first adsorption heat exchanger (51). The second discharge unit (102) is positioned closer to the second partition plate (75), and in front of the second adsorption heat exchanger (52) in the second heat exchanger chamber (38). That is, the second discharge unit (102) is positioned on the air outlet side of the second adsorption heat exchanger (52). The discharge units (101, 102) will be described in detail later.

Each adsorption heat exchanger (51, 52) stands in a corresponding one of the heat exchanger chambers (37, 38) so that the front and back faces of the adsorption heat exchanger (51, 52) are parallel to the upstream partition plate (71) and the downstream partition plate (72). That is, the adsorption heat exchangers (51, 52) are disposed so as to extend laterally across the heat exchanger chambers (37, 38), respectively. Each heat exchanger chamber (37, 38) is divided into front and rear spaces by a corresponding one of the adsorption heat exchangers (51, 52). In each heat exchanger chamber (37, 38), the adsorption heat exchanger (51, 52) is disposed at a position that is offset from the center in the longitudinal direction of the heat exchanger chamber (37, 38) toward the upstream partition plate (71). The adsorption heat exchangers (51, 52) are arranged substantially in a line in the lateral direction.

Each adsorption heat exchanger (51, 52) is provided with a liquid flow divider (61) and a gas header (62). The entire first adsorption heat exchanger (51), including the liquid flow divider (61) and the gas header (62), is accommodated in the first heat exchanger chamber (37). On the other hand, most of the second adsorption heat exchanger (52), including all fins (57), is accommodated in the second heat exchanger chamber (38), while a part of the second adsorption heat exchanger (52) extends through the central partition plate (73), and is exposed in the first heat exchanger chamber (37). Specifically, the liquid flow divider (61) and the gas header (62) of the second adsorption heat exchanger (52) are positioned in the first heat exchanger chamber (37). A U-tube portion (59) is positioned at an end of the second adsorption heat exchanger (52), to which the liquid flow divider (61) and the gas header (62) are connected. This U-tube portion (59) is also exposed in the first heat exchanger chamber (37). The electric expansion valve (55) of the refrigerant circuit (50) is accommodated in the first heat exchanger chamber (37).

A part of the internal space of the casing (11), which extends along the front face of the downstream partition plate (72), is divided into upper and lower spaces (see FIGS. 2, 3, and 5). Of these spaces, the upper space forms a supply air passage (31), and the lower space forms a discharge air passage (33).

The upstream partition plate (71) is provided with four open/close dampers (41-44) (see FIGS. 3 and 5). Each damper (41-44) has a substantially rectangular shape whose longer side extends in the lateral direction. Each damper (41-44) is configured to be able to open and close a corresponding air passage on the inlet side of a corresponding one of the adsorption heat exchangers (51, 52). Specifically, a first room air damper (41) and a second room air damper (42) are attached to a part (an upper part) of the upstream partition plate (71), which faces the room air passage (32). The first room air damper (41) is positioned on the right side of the central partition plate (73), and the second room air damper (42) is positioned on the left side of the central partition plate (73). A first outside air damper (43) and a second outside air damper (44) are attached to a part (a lower part) of the upstream partition plate (71), which faces the outside air passage (34). The first outside air damper (43) is positioned on the right side of the central partition plate (73), and the second outside air damper (44) is positioned on the left side of the central partition plate (73).

The room air passage (32) and the first heat exchanger chamber (37) are connected to, and disconnected from each other by opening and closing the first room air damper (41). The room air passage (32) and the second heat exchanger chamber (38) are connected to, and disconnected from each other by opening and closing the second room air damper (42). The outside air passage (34) and the first heat exchanger chamber (37) are connected to, and disconnected from each other by opening and closing the first outside air damper (43). The outside air passage (34) and the second heat exchanger chamber (38) are connected to, and disconnected from each other by opening and closing the second outside air damper (44).

In the upstream partition plate (71), the first outside air damper (43) is positioned directly under the first room air damper (41). The first room air damper (41) and the first outside air damper (43) are positioned so that their respective centers in the lateral direction are offset from the center in the lateral direction of the first heat exchanger chamber (37) toward the central partition plate (73) (i.e., toward the second side panel portion (15)) (see FIG. 3).

In the upstream partition plate (71), the second outside air damper (44) is positioned directly under the second room air damper (42). The second room air damper (42) and the second outside air damper (44) are positioned so that their respective centers in the lateral direction are offset from the center in the lateral direction of the second heat exchanger chamber (38) toward the central partition plate (73) (i.e., toward the first side panel portion (14)) (see FIG. 3).

The downstream partition plate (72) is provided with four open/close dampers (45-48) (see FIGS. 3 and 5). Each damper (45-48) has a substantially rectangular shape whose longer side extends in the lateral direction. Each damper (45-48) is configured to be able to open and close a corresponding air passage on the outlet side of a corresponding one of the adsorption heat exchangers (51, 52). Specifically, a first supply air damper (45) and a second supply air damper (46) are attached to a part (an upper part) of the downstream partition plate (72), which faces the supply air passage (31). The first supply air damper (45) is positioned on the right side of the central partition plate (73), and the second supply air damper (46) is positioned on the left side of the central partition plate (73). A first discharge air damper (47) and a second discharge air damper (48) are attached to a part (a lower part) of the downstream partition plate (72), which faces the discharge air passage (33). The first discharge air damper (47) is positioned on the right side of the central partition plate (73), and the second discharge air damper (48) is positioned on the left side of the central partition plate (73).

The supply air passage (31) and the first heat exchanger chamber (37) are connected to, and disconnected from each other by opening and closing the first supply air damper (45). The supply air passage (31) and the second heat exchanger chamber (38) are connected to, and disconnected from each other by opening and closing the second supply air damper (46). The discharge air passage (33) and the first heat exchanger chamber (37) are connected to, and disconnected from each other by opening and closing the first discharge air damper (47). The discharge air passage (33) and the second heat exchanger chamber (38) are connected to, and disconnected from each other by opening and closing the second discharge air damper (48).

In the downstream partition plate (72), the first discharge air damper (47) is positioned directly under the first supply air damper (45). The first supply air damper (45) and the first discharge air damper (47) are positioned so that their respective centers in the lateral direction are offset from the center in the lateral direction of the first heat exchanger chamber (37) toward the central partition plate (73) (i.e., toward the second side panel portion (15)) (see FIG. 3).

In the downstream partition plate (72), the second discharge air damper (48) is positioned directly under the second supply air damper (46). The second discharge air damper (48) and the second supply air damper (46) are positioned so that their respective centers in the lateral direction are offset from the center in the lateral direction of the second heat exchanger chamber (38) toward the central partition plate (73) (i.e., toward the first side panel portion (14)) (see FIG. 3).

The above dampers (41-48) form a switching unit capable of switching flow paths of the air flowing in the air passages in the casing (11). The dampers (41-48) also form a closed space forming unit for forming a closed space around each adsorption heat exchanger (51, 52) so as to hermetically seal the adsorption heat exchangers (51, 52) therein, when all the dampers are closed.

In the casing (11), the space between the supply air passage (31) and the discharge air passage (33), and the front panel portion (12) is divided by the partition plate (77) into right and left spaces. Of these spaces, the right space (the space on the right side of the partition plate (77)) forms an air supply fan chamber (36), and the left space (the space on the left side of the partition plate (77)) forms an air discharge fan chamber (35). This partition plate (77) stands at a position closer to the second side panel portion (15) than the central partition plate (73) is. Each of the air supply fan chamber (36) and the air discharge fan chamber (35) is a space that extends from the bottom plate of the casing (11) to the top plate thereof.

An air supply fan (26) is accommodated in the air supply fan chamber (36). An air discharge fan (25) is accommodated in the air discharge fan chamber (35). Each of the air supply fan (26) and the air discharge fan (25) is a centrifugal multi-blade fan (a so-called "sirocco fan").

Specifically, each fan (25, 26) includes a fan rotor, a fan casing (86), and a fan motor (89). Although not shown in the figures, the fan rotor has a cylindrical shape having an axial length shorter than the diameter thereof, and a multiplicity of blades are formed on the peripheral side surface thereof. The fan rotor is accommodated in the fan casing (86). An air inlet (87) is formed in one of side surfaces (the side surfaces extending perpendicularly to the axial direction of the fan rotor) of the fan casing (86). The fan casing (89) has a portion formed so as to protrude outward from a peripheral side surface thereof, and an air outlet (88) is formed at a protruding end of the portion. The fan motor (89) is attached to a side surface of the fan casing (86), which is located on a side opposite to the air inlet (87). The fan motor (89) is connected to the fan rotor to rotation drive the fan rotor.

In each of the air supply fan (26) and the air discharge fan (25), when the fan rotor is rotation driven by the fan motor (89), air is drawn into the fan casing (86) through the air inlet (87), and air in the fan casing (86) is discharged out of the fan casing (86) through the air outlet (88).

In the air supply fan chamber (36), the air supply fan (26) is disposed so that the air inlet (87) of the fan casing (86) faces the downstream partition plate (72). The air outlet (88) of the fan casing (86) of the air supply fan (26) is attached to the first side panel portion (14) so as to communicate with the air supply port (22).

In the air discharge fan chamber (35), the air discharge fan (25) is disposed so that the air inlet (87) of the fan casing (86) faces the downstream partition plate (72). The air outlet (88) of the fan casing (86) of the air discharge fan (25) is attached to the second side panel portion (15) so as to communicate with the air discharge port (21).

The compressor (53) and the four-way selector valve (54) of the refrigerant circuit (50) are accommodated in the air supply fan chamber (36). The compressor (53) and the four-way selector valve (54) are positioned between the air supply fan (26) and the partition plate (77) in the air supply fan chamber (36).

Connecting pipes (65), each extending from the gas header (62) of a corresponding one of the adsorption heat exchangers (51, 52), are connected to the four-way selector valve (54). The connecting pipes (65) extend through the downstream partition plate (72). Specifically, a part (an upper part) of the downstream partition plate (72) faces the supply air passage (31), and the connecting pipes (65) extend through a part of this upper part, which is located on the right side of the central partition wall (73) (that is, a part facing the first heat exchanger chamber (37)). Note that one of the respective liquid flow dividers (61) of the adsorption heat exchangers (51, 52) is connected to one end of the electric expansion valve (55), and the other liquid flow divider (61) is connected to the other end of the electric expansion valve (55).

In the casing (11), the space between the first partition plate (74) and the first side panel portion (14) forms a first bypass passage (81), which is a first sub air passage (see FIGS. 2 and 3). In the casing (11), the space between the second partition plate (75) and the second side panel portion (15) forms a second bypass passage (82), which is a second sub air passage (see FIGS. 3 and 4). Each of the first bypass passage (81) and the second bypass passage (82) is a space that extends from the bottom plate of the casing (11) to the top plate thereof.

A starting end of the first bypass passage (81) (an end located on the back panel portion (13) side) communicates only with the outside air passage (34), and is disconnected from the room air passage (32). The first bypass passage (81) communicates with a part of the outside air passage (34), which is located downstream of the outside air filter (28). A terminal end of the first bypass passage (81) (an end located on the front panel portion (12) side) is separated from the supply air passage (31), the discharge air passage (33), and the air supply fan chamber (36) by a partition plate (78). A first bypass damper (83) is provided on a part of the partition plate (78), which faces the air supply fan chamber (36). The first bypass damper (83) has a substantially rectangular shape whose longer side extends in the vertical direction. The first bypass passage (81) and the air supply fan chamber (36) are connected to, and disconnected from each other by opening and closing the first bypass damper (83).

A starting end of the second bypass passage (82) (an end located on the back panel portion (13) side) communicates only with the room air passage (32), and is disconnected from the outside air passage (34). The second bypass passage (82) communicates with a part of the room air passage (32), which is located downstream of the room air filter (27), via a communication hole (76) formed in the second partition plate (75). A terminal end (an end located on the front panel portion (12) side) of the second bypass passage (82) is separated from the supply air passage (31), the discharge air passage (33), and the air discharge fan chamber (35) by a partition plate (79). A second bypass damper (84) is provided in a part of the partition plate (79), which faces the discharge air fan chamber (35). The second bypass damper (84) has a substantially rectangular shape whose longer side extends in the vertical direction. The second bypass passage (82) and the discharge air fan chamber (35) are connected to, and disconnected from each other by opening and closing the second bypass damper (84).

Note that the first bypass passage (81), the second bypass passage (82), the first bypass damper (83), and the second bypass damper (84) are not shown in the right and left side views in FIG. 5.

In the humidity control system (10), the first bypass damper (83), the second bypass damper (84), the first supply air damper (45), the second supply air damper (46), the first discharge air damper (47), and the second discharge air damper (48) form a switching mechanism. That is, when the first supply air damper (45), the second supply air damper (46), the first discharge air damper (47), and the second discharge air damper (48) are closed, and the first bypass damper (83) and the second bypass damper (84) are open, air flowing in the casing (11) passes through the first bypass passage (81) or the second bypass passage (82) without passing through the first heat exchanger chamber (37) and the second heat exchanger chamber (38). When the first bypass damper (83) and the second bypass damper (84) are closed, and one supply air damper (45, 46) and one discharge air damper (47, 48) are open, the air flowing in the casing (11) passes through the first heat exchanger chamber (37) or the second heat exchanger chamber (38) without passing through the first bypass passage (81) and the second bypass passage (82).

A part of the first side panel portion (14) of the casing (11), which face the room air passage (32) and the outside air passage (34), is formed by a filter open/close panel (17). A part of the first side panel portion (14), which faces the first bypass passage (81), is formed by a main open/close panel (16). The filter open/close panel (17) and the main open/close panel (16) are detachable from the casing (11).

An electrical equipment box (90) is attached to a right part of the front panel portion (12) of the casing (11). Note that the electrical equipment box (90) is not shown in FIGS. 2 and 5. The electrical equipment box (90) is a rectangular parallelepiped-shaped box, and a control substrate (91) and a power supply substrate (92) are accommodated in the electrical equipment box (90). The control substrate (91) and the power supply substrate (92) are attached to the inner surface of one of side plates of the electrical equipment box (90), which is a side plate (a back plate) that adjoins the front panel portion (12). A cooling fin (93) is provided in an inverter section of the power supply substrate (92). This cooling fin (93) is provided so as to protrude from the back surface of the power supply substrate (92). The cooling fin (93) extends through the back plate of the electrical equipment box (90) and the front panel portion (12) of the casing (11), and is exposed in the air apply fan chamber (36) (see FIGS. 3 and 4).

Lead wires, which connect to the compressor (53), the fans (25, 26), the dampers (41-48), the humidity sensors (96, 97), and the like in the casing (11), extend into the electrical equipment box (90). Of these lead wires, lead wires connecting to drive motors for the dampers (41-44) attached to the upstream partition plate (71), and lead wires connecting to the humidity sensors (96, 97) extend through the first bypass passage (81) into the electrical equipment box (90).

[Configuration of the Refrigerant Circuit]

Figure 6:
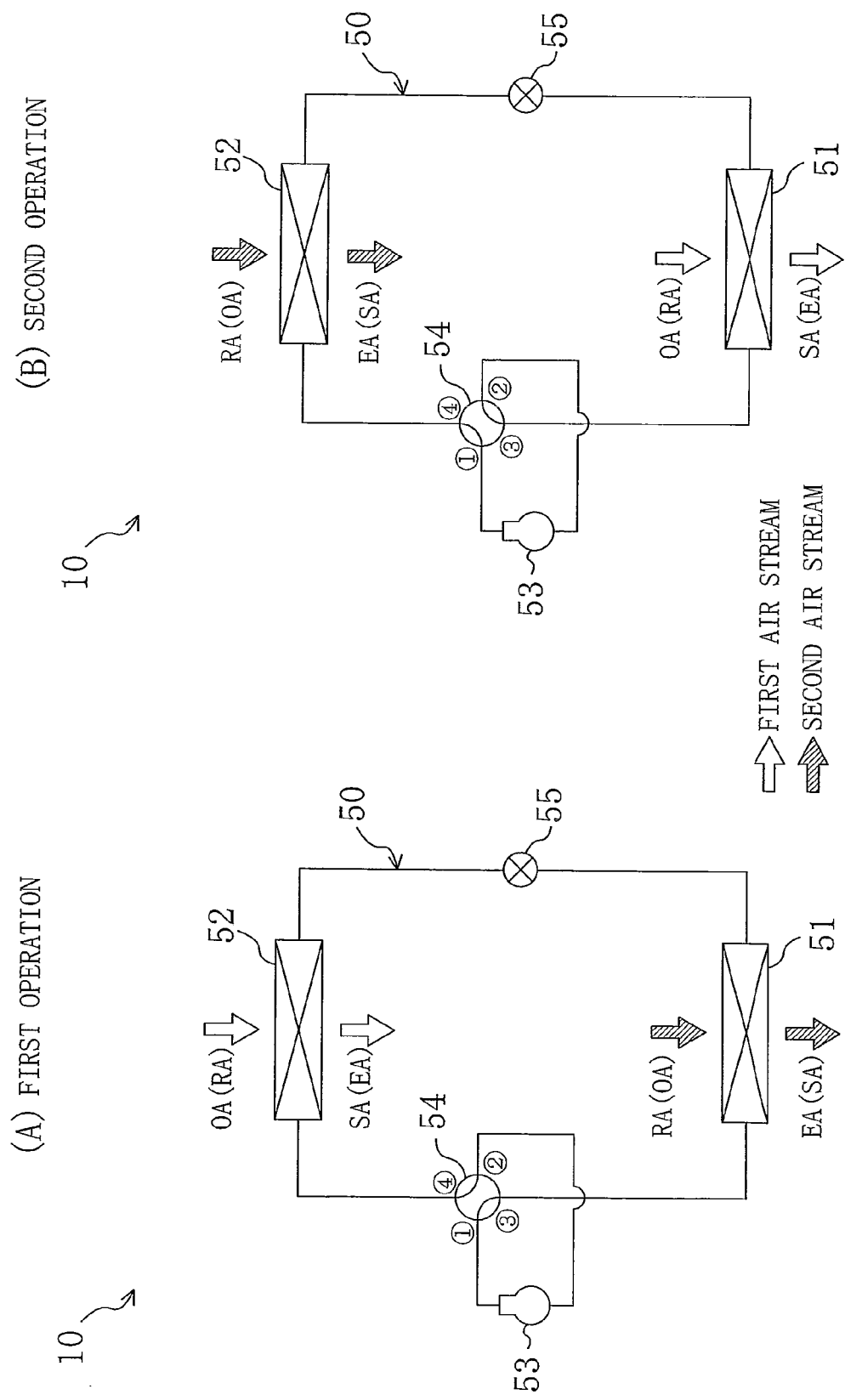
FIG. 6 shows piping diagrams showing the configuration of a refrigerant circuit, where

The refrigerant circuit (50) will be described below with reference to FIG. 6.

The refrigerant circuit (50) is a closed circuit provided with the first adsorption heat exchanger (51), the second adsorption heat exchanger (52), the compressor (53), the four-way selector valve (54), and the electric expansion valve (55). This refrigerant circuit (50) performs a vapor compression refrigeration cycle by circulating a refrigerant filling the refrigerant circuit (50).

In the refrigerant circuit (50), the outlet side of the compressor (53) is connected to a first port of the four-way selector valve (54), and the inlet side of the compressor (53) is connected to a second port of the four-way selector valve (54). One end of the first adsorption heat exchanger (51) is connected to a third port of the four-way selector valve (54). The other end of the first adsorption heat exchanger (51) is connected to one end of the second adsorption heat exchanger (52) via the electric expansion valve (55). The other end of the second adsorption heat exchanger (52) is connected to a fourth port of the four-way selector valve (54).

The four-way selector valve (54) is switchable between a first state where the first and third ports communicate with each other, and the second and fourth ports communicate with each other (a state shown in FIG. 6(A)), and a second state where the first and fourth ports communicate with each other, and the second and third ports communicate with each other (a state shown in FIG. 6(B)).

Figure 7:
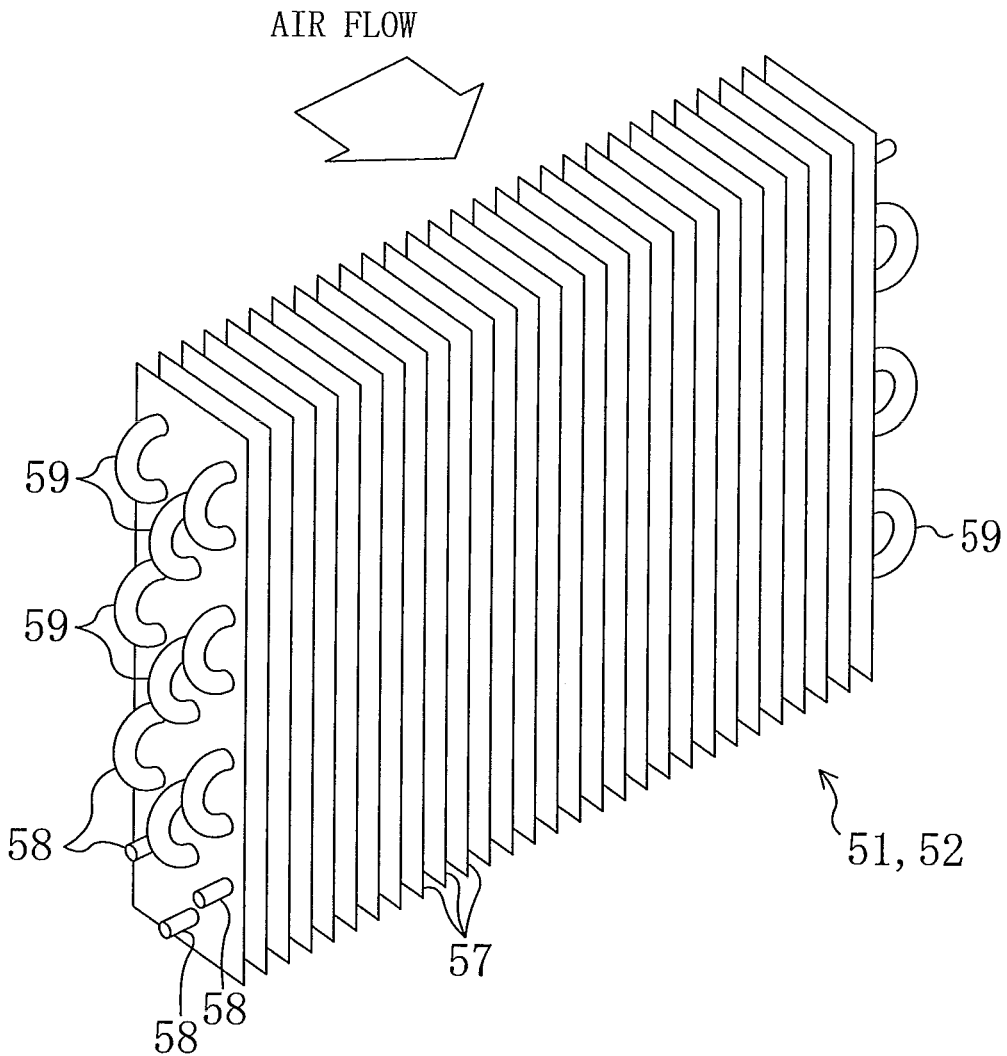
FIG. 7 is a schematic perspective view of an adsorption heat exchanger.

As shown in FIG. 7, each of the first adsorption heat exchanger (51) and the second adsorption heat exchanger (52) is formed by a cross-fin type fin-and-tube heat exchanger. Each of these adsorption heat exchangers (51, 52) includes a copper heat transfer tube (58), and aluminum fins (57). The plurality of fins (57) are arranged at regular intervals in the adsorption heat exchanger (51, 52), and each fin (57) has a rectangular plate shape. The heat transfer tube (58) is shaped so as to meander in the direction in which the fins (57) are arranged. That is, straight tube parts, extending through the fins (57), and U-tube parts (59), each connecting adjacent ones of the straight tube parts, are alternately formed in this heat transfer tube (58).

Each adsorption heat exchanger (51, 52) forms an adsorption member having an adsorbent supported on the surface of each fin (57). In each adsorption heat exchanger (51, 52), air passing between the fins (57) contacts the adsorbent supported on the fins (57). Thus, the adsorbent adsorbs moisture contained in the air, or releases (desorbs) moisture, which has been adsorbed by the adsorbent, into the air. A material capable of adsorbing water vapor contained in the air, such as zeolite, silica gel, activated carbon, or an organic polymer material having hydrophilic functional groups, is used as the adsorbent.

In the humidity control system (10) of the present embodiment, the refrigerant circuit (50) forms a heat transfer medium circuit. In this refrigerant circuit (50), a high pressure gas refrigerant is supplied as a heating heat transfer fluid to one of the two adsorption heat exchangers (51, 52), which operates as a condenser. A low pressure gas-liquid two-phase refrigerant is supplied as a cooling heat transfer fluid to the other adsorption heat exchanger operating as an evaporator.

[Configuration of the Discharge Units]

Each discharge unit (101, 102) described above forms an active species generating unit for supplying active species to a corresponding one of the heat exchanger chambers (37, 38) as a closed space. That is, the first discharge unit (101) supplies active species to the first heat exchanger chamber (37), and the second discharge unit (102) supplies active species to the second heat exchanger chamber (38).

Figure 8:
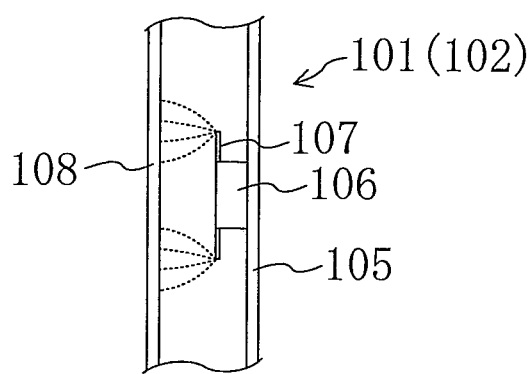
FIG. 8 is a side view showing a main part of a discharge unit.

Each discharge unit (101, 102) forms a streamer discharge apparatus for generating active species by generating a streamer discharge. Specifically, as shown in FIG. 8, each discharge unit (101, 102) has a discharge-side support plate (105), an electrode support (106), a discharge electrode (107), and a counter electrode (108).

The discharge-side support plate (105) has a long flat plate shape. The discharge-side support plate (105) is supported in the heat exchanger chamber (37, 38) so as to extend vertically. The electrode support portion (106) is provided on the discharge-side support plate (105) so as to protrude from a flat surface portion on one side of the discharge-side support plate (105). The bar-shaped or linear discharge electrode (107) is supported at the end of the electrode support portion (106). The discharge electrode (107) extends vertically so as to be parallel to the discharge-side support plate (105). The discharge electrode (107) is made of e.g., a tungsten material.

The counter electrode (108) has a long flat plate shape. The counter electrode (108) is supported in the heat exchanger chamber (37, 38) so as to face the discharge-side support plate (105) and the discharge electrode (107). A flat surface portion of the counter electrode (108) extends parallel to the discharge electrode (107). That is, a uniform gap (e.g., 5 mm) is maintained between the counter electrode (108) and the discharge electrode (107) in their longitudinal direction.

A power source, not shown, is connected to each discharge unit (101, 102). The positive side of the power source is electrically connected to the discharge electrode (107), and the earth side (or the negative side) thereof is electrically connected to the counter electrode (108). When a predetermined voltage is applied from the power source to the discharge electrode (107) and the counter electrode (108), a streamer discharge is generated from the discharge electrode (107) toward the counter electrode (108).

In the first discharge unit (101), the direction from the discharge electrode (107) toward the counter electrode (108), in which the discharge is generated (the direction in which a plasma is developed) faces toward the first adsorption heat exchanger (51) or the central partition plate (73). In the second discharge unit (102), the direction from the discharge electrode (107) toward the counter electrode (108), in which the discharge is generated (the direction in which a plasma is developed) faces toward the second adsorption heat exchanger (52) or the central partition plate (73). The behavior of the streamer discharge in the discharge unit (101, 102) will be described in detail later.

[Operation in Each Operation Mode]

The humidity control system (10) of the present embodiment operates in a dehumidification/ventilation mode and a humidification/ventilation mode. In the dehumidification/ventilation mode and the humidification/ventilation mode, the humidity control system (10) controls the humidity of intake outside air (OA) to supply the resultant air into a room as supply air (SA), and, at the same time, discharges intake room air (RA) out of the room as exhaust air (EA). On the other hand, in a simple ventilation mode, the hydraulic control system (10) supplies intake outside air (OA) into the room as it is as supply air (SA), and, at the same time, discharges intake room air (RA) out of the room as it is as exhaust air (EA)

(Dehumidification/Ventilation Mode)

In the dehumidification/ventilation mode, the humidity control system (10) repeats a first operation and a second operation, which will be described later, alternately at predetermined time intervals (e.g., at intervals of three minutes). In the dehumidification/ventilation mode, the first bypass damper (83) and the second bypass damper (84) are closed all the time.

In the dehumidification/ventilation mode, when the air supply fan (26) is operated in the humidity control system (10), outside air is drawn into the casing (11) through the outside air intake port (24) as a first air stream. When the air discharge fan (25) is operated, room air is drawn into the casing (11) through the room air intake port (23) as a second air stream.

Figure 9:
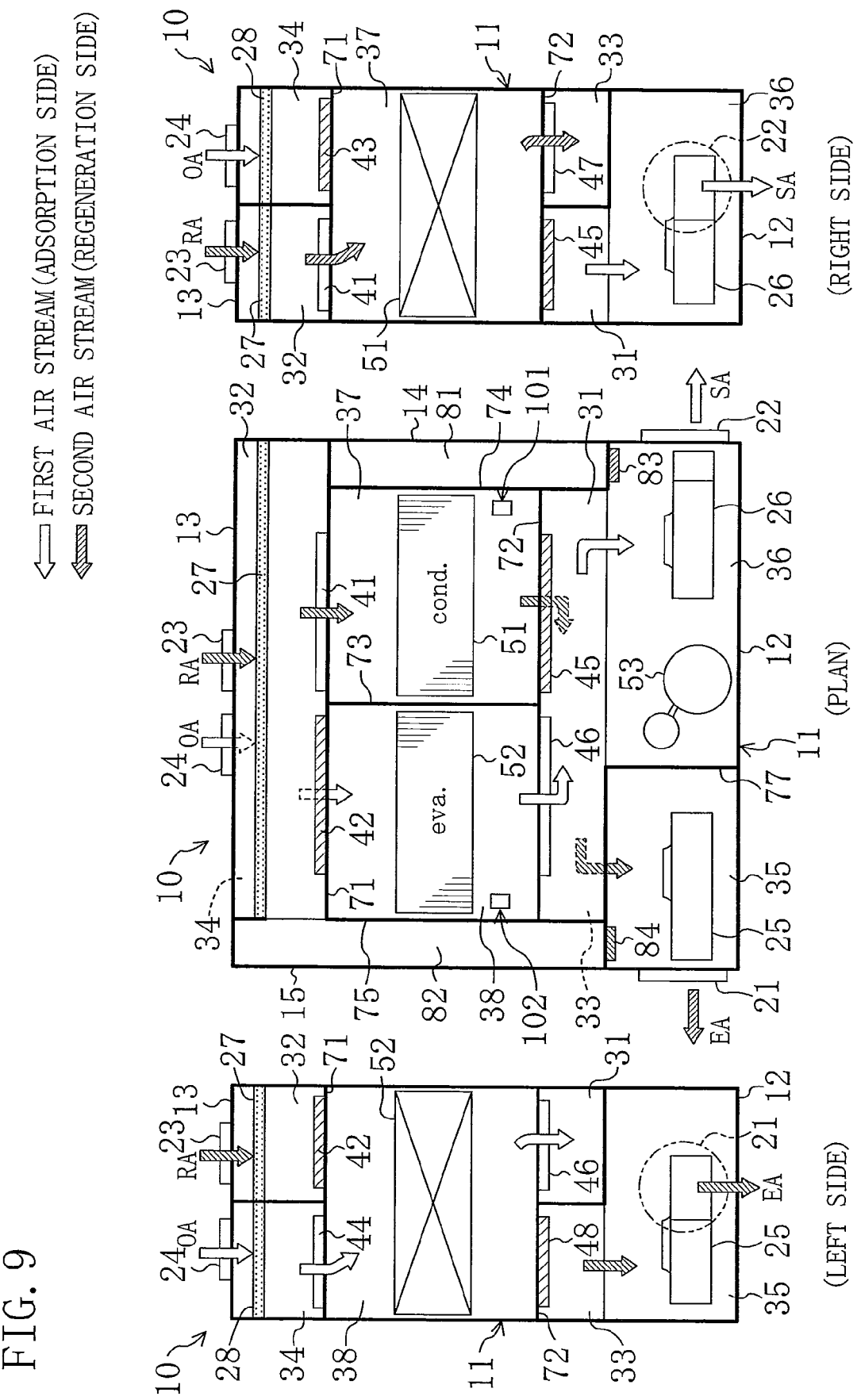
FIG. 9 shows a schematic plan view, and schematic right and left side views of the humidity control system, illustrating air flows in a first operation in a dehumidification/ventilation mode.

First, the first operation in the dehumidification/ventilation mode will be described. As shown in FIG. 9, in the first operation, the first room air damper (41), the second outside air damper (44), the second supply air damper (46), and the first discharge air damper (47) are opened, and the second room air damper (42), the first outside air damper (43), the first supply air damper (45), and the second discharge air damper (48) are closed.

During the first operation, as shown in FIG. 6(A), the four-way selector valve (54) in the refrigerant circuit (50) is in the first state. In this state, the refrigerant circulates in the refrigerant circuit (50), whereby the refrigeration cycle is performed. At this time, in the refrigerant circuit (50), the refrigerant discharged from the compressor (53) sequentially passes through the first adsorption heat exchanger (51), the electric expansion valve (55), and the second adsorption heat exchanger (52) in this order, where the first adsorption heat exchanger (51) operates as a condenser, and the second adsorption heat exchanger (52) operates as an evaporator.

After flowing into the outside air passage (34) and through the outside air filter (28), the first air stream flows through the second outside air damper (44) into the second heat exchanger chamber (38), and then, flows through the second adsorption heat exchanger (52). In the second adsorption heat exchanger (52), moisture in the first air stream is adsorbed by the adsorbent, and adsorption heat generated by this adsorption is absorbed by the refrigerant. The first air stream dehumidified in the second adsorption heat exchanger (52) flows through the second supply air damper (46) into the supply air passage (31). Then, the first air stream flows through the air supply fan chamber (36), and is supplied into the room through the air supply port (22).

On the other hand, after flowing into the room air passage (32) and through the room air filter (27), the second air stream flows through the first room air damper (41) into the first heat exchanger chamber (37), and then, flows through the first adsorption heat exchanger (51). In the first adsorption heat exchanger (51), moisture is desorbed from the adsorbent heated by the refrigerant, and the desorbed moisture is applied to the second air stream. The second air stream humidified in the first adsorption heat exchanger (51) flows through the first discharge air damper (47) into the discharge air passage (33). Then, the second air stream flows through the air discharge fan chamber (35), and is discharged out of the room through the air discharge port (21).

Figure 10:
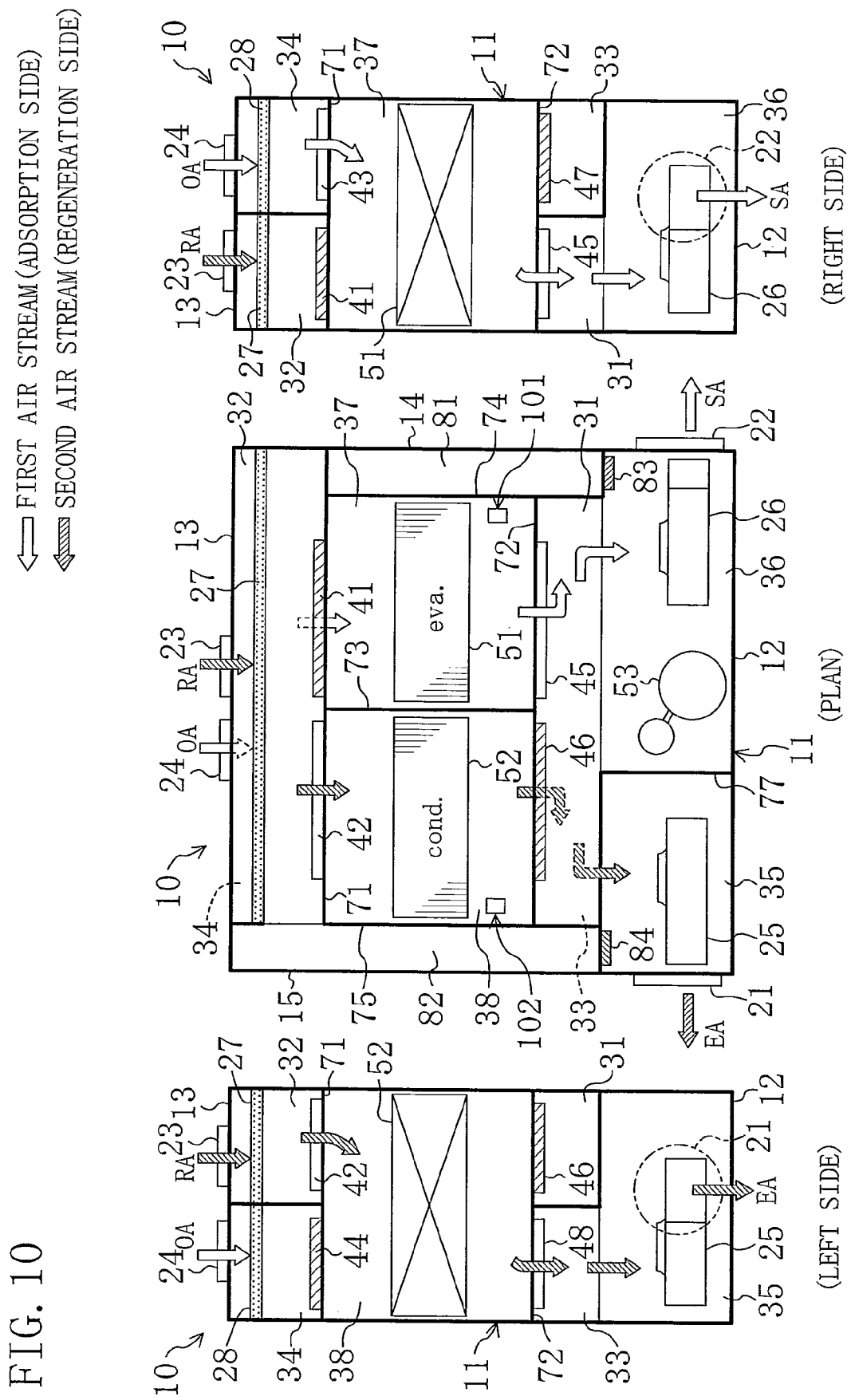
FIG. 10 shows a schematic plan view, and schematic right and left side views of the humidity control system, illustrating air flows in a second operation in the dehumidification/ventilation mode.

Next, the second operation in the dehumidification/ventilation mode will be described. As shown in FIG. 10, in the second operation, the second room air damper (42), the first outside air damper (43), the first supply air damper (45), and the second discharge air damper (48) are opened, and the first room air damper (41), the second outside air damper (44), the second supply air damper (46), and the first discharge air damper (47) are closed.

During the second operation, as shown in FIG. 6(B), the four-way selector valve (54) in the refrigerant circuit (50) is in the second state. In this state, the refrigerant circulates in the refrigerant circuit (50), whereby the refrigeration cycle is performed. At this time, in the refrigerant circuit (50), the refrigerant discharged from the compressor (53) sequentially passes through the second adsorption heat exchanger (52), the electric expansion valve (55), and the first adsorption heat exchanger (51) in this order, where the first adsorption heat exchanger (51) operates as an evaporator, and the second adsorption heat exchanger (52) operates as a condenser.

After flowing into the outside air passage (34) and through the outside air filter (28), the first air stream flows through the first outside air damper (43) into the first heat exchanger chamber (37), and then, flows through the first adsorption heat exchanger (51). In the first adsorption heat exchanger (51), moisture in the first air stream is adsorbed by the adsorbent, and adsorption heat generated by this adsorption is absorbed by the refrigerant. The first air stream dehumidified in the first adsorption heat exchanger (51) flows through the first supply air damper (45) into the supply air passage (31). Then, the first air stream flows through the air supply fan chamber (36), and is supplied into the room through the air supply port (22).

On the other hand, after flowing into the room air passage (32) and through the room air filter (27), the second air stream flows through the second room air damper (42) into the second heat exchanger chamber (38), and then, flows through the second adsorption heat exchanger (52). In the second adsorption heat exchanger (52), moisture is desorbed from the adsorbent heated by the refrigerant, and the desorbed moisture is applied to the second air stream. The second air stream humidified in the second adsorption heat exchanger (52) flows through the second discharge air damper (48) into the discharge air passage (33). Then, the second air stream flows through the air discharge fan chamber (35), and is discharged out of the room through the air discharge port (21).

(Humidification/Ventilation Mode)

In the humidification/ventilation mode, the humidity control system (10) repeats a first operation and a second operation, which will be described later, alternately at predetermined time intervals (e.g., at intervals of three minutes). In the humidification/ventilation mode, the first bypass damper (83) and the second bypass damper (84) are closed all the time.

In the humidification/ventilation mode, when the air supply fan (26) is operated in the humidity control system (10), outside air is drawn into the casing (11) through the outside air intake port (24) as a second air stream. When the air discharge fan (25) is operated, room air is drawn into the casing (11) through the room air intake port (23) as a first air stream.

Figure 11:
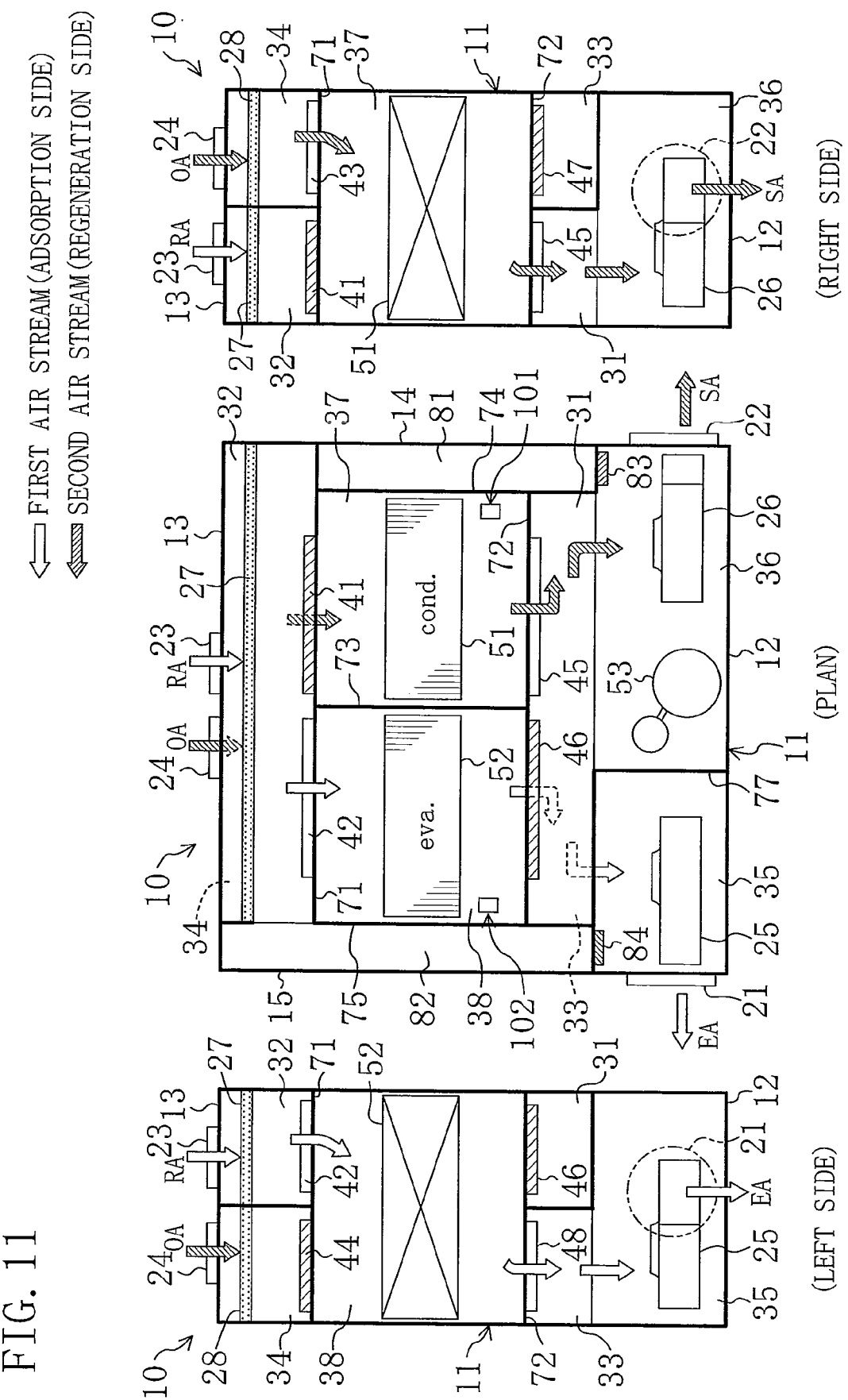
FIG. 11 shows a schematic plan view, and schematic right and left side views of the humidity control system, illustrating air flows in a first operation in a humidification/ventilation mode.

First, the first operation in the humidification/ventilation mode will be described. As shown in FIG. 11, in the first operation, the second room air damper (42), the first outside air damper (43), the first supply air damper (45), and the second discharge air damper (48) are opened, and the first room air damper (41), the second outside air damper (44), the second supply air damper (46), and the first discharge air damper (47) are closed.

During the first operation, as shown in FIG. 6(A), the four-way selector valve (54) in the refrigerant circuit (50) is in the first state. In the refrigerant circuit (50), the first adsorption heat exchanger (51) operates as a condenser, and the second adsorption heat exchanger (52) operates as an evaporator, as in the case of the first operation in the dehumidification/ventilation mode.

After flowing into the room air passage (32) and through the room air filter (27), the first air stream flows through the second room air damper (42) into the second heat exchanger chamber (38), and then, flows through the second adsorption heat exchanger (52). In the second adsorption heat exchanger (52), moisture in the first air stream is adsorbed by the adsorbent, and adsorption heat generated by this adsorption is absorbed by the refrigerant. The first air stream dehumidified in the second adsorption heat exchanger (52) flows through the second discharge air damper (48) into the discharge air passage (33). Then, the first air stream flows through the air discharge fan chamber (35), and is discharged out of the room through the air discharge port (21).

On the other hand, after flowing into the outside air passage (34) and through the outside air filter (28), the second air stream flows through the first outside air damper (43) into the first heat exchanger chamber (37), and then, flows through the first adsorption heat exchanger (51). In the first adsorption heat exchanger (51), moisture is desorbed from the adsorbent heated by the refrigerant, and the desorbed moisture is applied to the second air stream. The second air stream humidified in the first adsorption heat exchanger (51) flows through the first supply air damper (45) into the supply air passage (31). Then, the second air stream flows through the air supply fan chamber (36), and is supplied into the room through the air supply port (22).

Figure 12:
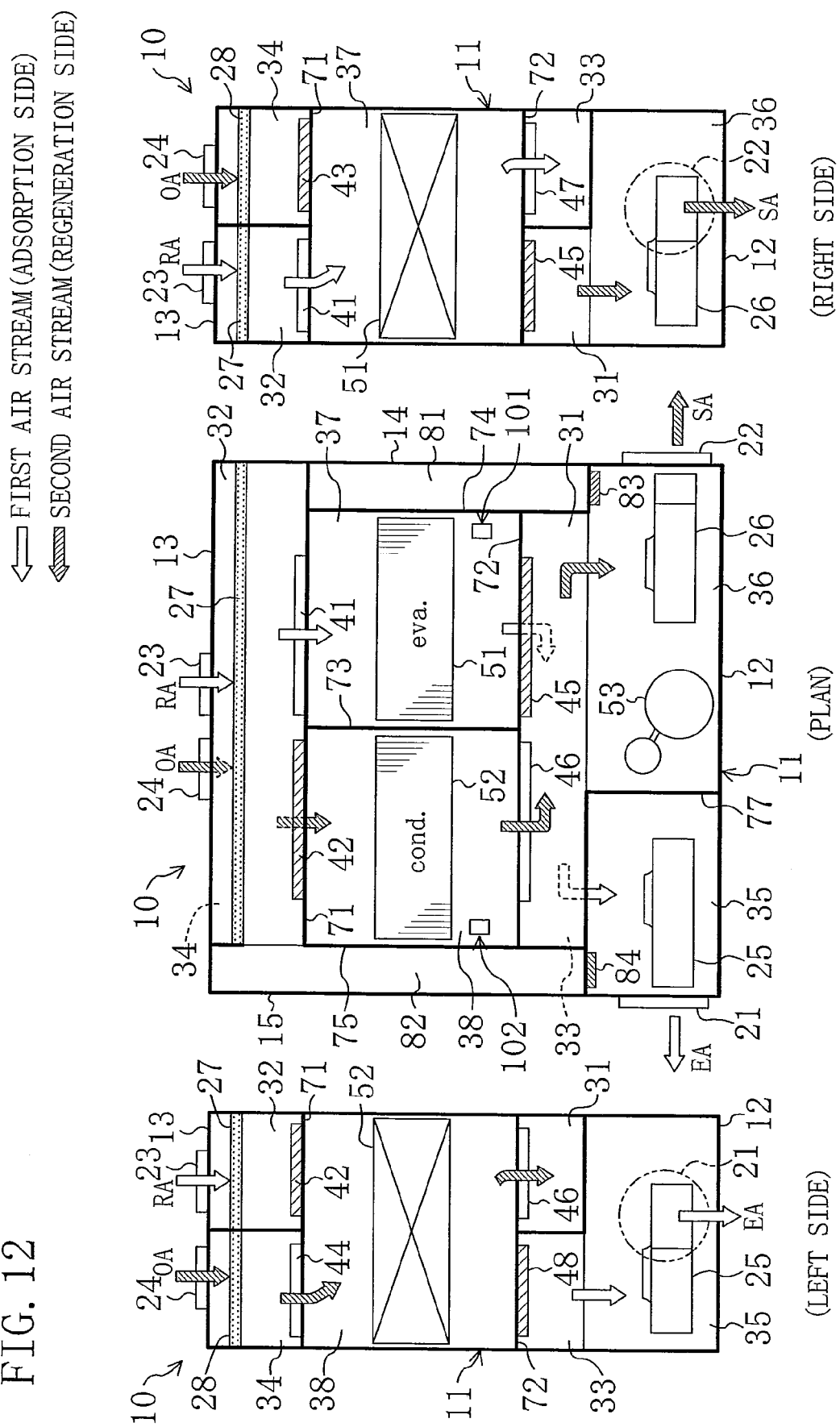
FIG. 12 shows a schematic plan view, and schematic right and left side views of the humidity control system, illustrating air flows in a second operation in the humidification/ventilation mode.

Next, the second operation in the humidification/ventilation mode will be described. As shown in FIG. 12, in the second operation, the first room air damper (41), the second outside air damper (44), the second supply air damper (46), and the first discharge air damper (47) are opened, and the second room air damper (42), the first outside air damper (43), the first supply air damper (45), and the second discharge air damper (48) are closed.

During the second operation, as shown in FIG. 6(B), the four-way selector valve (54) in the refrigerant circuit (50) is in the second state. In the refrigerant circuit (50), the first adsorption heat exchanger (51) operates as an evaporator, and the second adsorption heat exchanger (52) operates as a condenser, as in the case of the second operation in the dehumidification/ventilation mode.

After flowing into the room air passage (32) and through the room air filter (27), the first air stream flows through the first room air damper (41) into the first heat exchanger chamber (37), and then, flows through the first adsorption heat exchanger (51). In the first adsorption heat exchanger (51), moisture in the first air stream is adsorbed by the adsorbent, and adsorption heat generated by this adsorption is absorbed by the refrigerant. The first air stream dehumidified in the first adsorption heat exchanger (51) flows through the first discharge air damper (47) into the discharge air passage (33). Then, the first air stream flows through the air discharge fan chamber (35), and is discharged out of the room through the air discharge port (21).

On the other hand, after flowing into the outside air passage (34) and through the outside air filter (28), the second air stream flows through the second outside air damper (44) into the second heat exchanger chamber (38), and then, flows through the second adsorption heat exchanger (52). In the second adsorption heat exchanger (52), moisture is desorbed from the adsorbent heated by the refrigerant, and the desorbed moisture is applied to the second air stream. The second air stream humidified in the second adsorption heat exchanger (52) flows through the second supply air damper (46) into the supply air passage (31). Then, the second air stream flows through the air supply fan chamber (36), and is supplied into the room through the air supply port (22).

(Operation when the System is Stopped)

Incidentally, when the humidity control system (10) continuously operates in a mode such as the dehumidification/ventilation mode and the humidification/ventilation mode described above (hereinafter referred to as the "humidity control mode"), odorous components can be adsorbed by the adsorbent of each adsorption heat exchanger (51, 52). Specifically, when the humidity control system (10) takes room air, containing odorous components such as, e.g., a tobacco odor or ammonia, therein to discharge the room air out of the room, these odorous components are adsorbed by the adsorbent of each adsorption heat exchanger (51, 52). As a result, the odorous components can be accumulated and concentrated in the adsorbent of each adsorption heat exchanger (51, 52).

If the humidity control mode is resumed in this state, the odorous components can be desorbed from the adsorbent and supplied into the room, depending on the operating conditions. Specifically, if, e.g., outside air having extremely high humidity passes the adsorbent, moisture in the air can be adsorbed by the adsorbent so as to be replaced with the odorous components. In this case, a high concentration of odorous components is desorbed from the adsorbent. As a result, a relatively high concentration of odorous components is supplied into the room, making the room very uncomfortable.

Thus, the humidity control system (10) of the present embodiment performs the following operation (an odor decomposition operation) when the humidity control system (10) is stopped, in order to prevent accumulation of odorous components in the adsorbent of each adsorption heat exchanger (51, 52).

Figure 14:
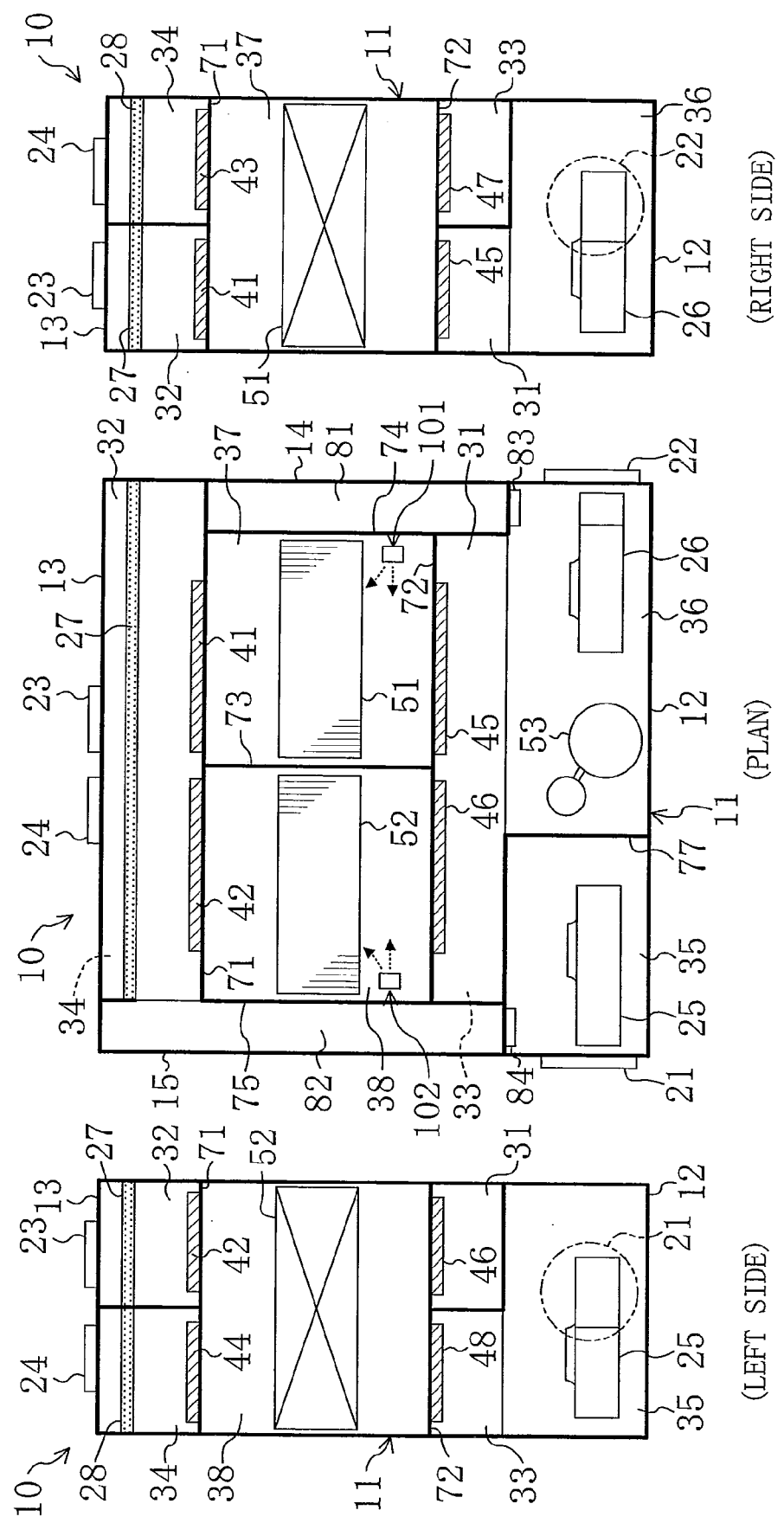
FIG. 14 shows a schematic plan view, and schematic right and left side views of the humidity control system when the humidity control system is off.

As shown in FIG. 13(A), when a command to stop (turn off) the humidity control system (10) is received from, e.g., an operation section (such as a remote control unit) operated by the user or the like (step S1), the compressor (53), the air discharge fan (25), and the air supply fan (26) are stopped (step S2). After step S2, all the dampers (41-48) around each heat exchanger chamber (37, 38) are closed (step S3). As a result, the first heat exchanger chamber (37) becomes a closed space that hermetically seals the first adsorption heat exchanger (51) therein, and the second heat exchanger chamber (38) becomes a sealed space that hermetically seals the second adsorption heat exchanger (52) therein. That is, each heat exchanger chamber (37, 38) is completely disconnected from the outside thereof (see FIG. 14).

After step S3, a streamer discharge is generated by the first discharge unit (101) and the second discharge unit (102) (step S4). Specifically, in each discharge unit (101, 102), a voltage is applied from the power source to the discharge electrode (107) and the counter electrode (108). As a result, a streamer discharge occurs toward the counter electrode (108) in each discharge unit (101, 102), with both longitudinal ends of the discharge electrode (107) serving as a base point of the discharge. More specifically, micro arcs are continuously developed in a flared shape from both ends of the discharge electrode (107), respectively, forming plasma columns with light emission. With such a streamer discharge, active species are generated in a discharge field in the air. Note that examples of the active species include fast electrons, ions, ozone, radicals such as hydroxy radicals, and other excited molecules (such as excited oxygen molecules, excited nitrogen molecules, and excited water molecules).

When the streamer discharge is generated, an ionic wind is generated in each discharge unit (101, 102). This ionic wind blows in substantially the same direction as the direction in which the streamer discharge occurs. Thus, in the first discharge unit (101), an air current is produced toward the first adsorption heat exchanger (51) or the central partition plate (73). In the second discharge unit (102), an air current is produced toward the second adsorption heat exchanger (52) or the central partition plate (73).

In each heat exchanger chamber (37, 38), the above active species contact the adsorbent of each adsorption heat exchanger (51, 52) while being carried by the ionic wind. Thus, the odorous components adsorbed by the adsorbent are decomposed by oxidation with the active species. At this time, since each heat exchanger chamber (37, 38) is a closed space, no active species leaks out of the heat exchanger chambers (37, 38). Thus, the concentration of the active species is increased, and the odorous components are efficiently decomposed.

(Operation when the System is Restarted)

However, in the above odor decomposition operation, unreacted active species can remain in each heat exchanger chamber (37, 38) as a closed space. If the humidity control mode is resumed in this state, the remaining active species can be supplied into the room, causing disadvantages. Thus, the humidity control system (10) of the present embodiment operates in an outside air circulation mode (a purge operation) after the above odor decomposition operation. The outside air circulation mode is a mode of discharging air in each heat exchanger chamber (37, 38) out of the room before the humidity control mode is resumed.

As shown in FIG. 13(B), when a command to start (turn on) the humidity control system (10) is received from, e.g., the operation section (such as a remote control unit) operated by the user or the like (step S11), the streamer discharge in each discharge unit (101, 102) is stopped, and the odor decomposition operation is terminated (step S12). After step S12, the control flow proceeds to the outside air circulation mode described below.

Figure 15:
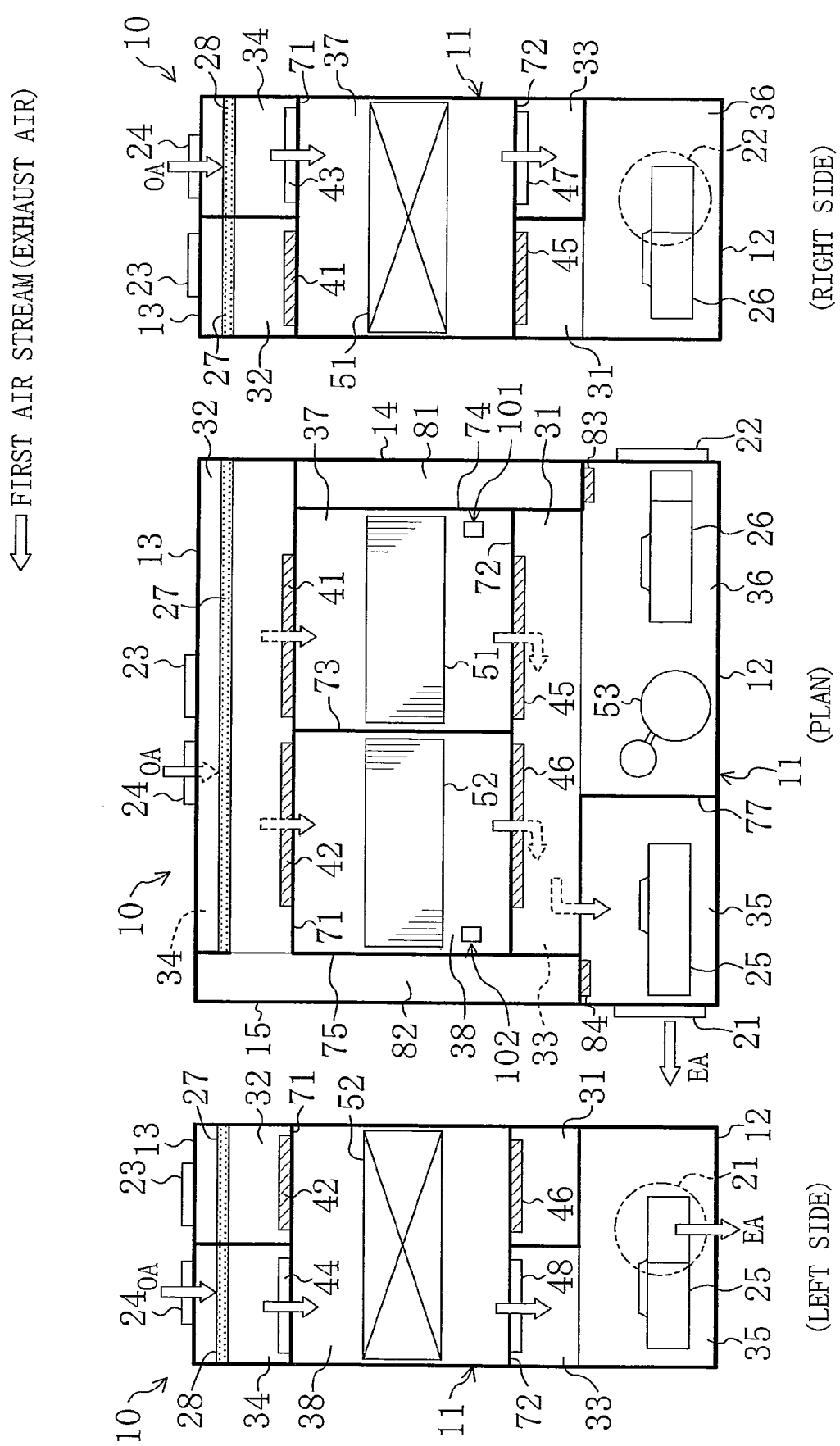
FIG. 15 shows a schematic plan view, and schematic right and left side views of the humidity control system, illustrating air flows in an outside air circulation mode.

In the outside air circulation mode, the first room air damper (41), the second room air damper (42), the first supply air damper (45), and the second supply air damper (46) are closed, and the first outside air damper (43), the second outside air damper (44), and the first discharge air damper (47), and the second discharge air damper (48) are opened. That is, only the outside air dampers (43, 44, 47, 48), which open and close the respective air passages leading to the outside of the room, are opened in the outside air circulation mode (step S13; see FIG. 15). Then, in step S14, only the air discharge fan (25) is driven, and the air supply fan (26) is kept stopped. Thus, outside air is drawn into the casing (11) through the outside air intake port (24) as a first air stream.

The first air stream flowing into the outside air passage (34) divides into two air streams. One of the two air streams flows through the first outside air damper (43) into the first heat exchanger chamber (37), while the other flows through the second outside air damper (44) into the second heat exchanger chamber (38). The air stream, which has flown into the first heat exchanger chamber (37), flows through the first discharge air damper (47) into the discharge air passage (33), while taking the remaining active species therein. The air stream, which has flown into the second heat exchanger chamber (38), flows through the second discharge air damper (48) into the discharge air passage (33), while taking the remaining active pieces therein. These air streams merge in the discharge air passage (33), and the merged air flows through the discharge air fan chamber (35), and then, is discharged out of the room through the air discharge port (21).

The above outside air circulation mode enables the active species remaining in the heat exchanger chambers (37, 38) to be reliably discharged out of the room. After a predetermined time has passed since the start of the outside air circulation mode, the outside air circulation mode is terminated, and the humidity control system operates in the above normal humidity control mode.

Effects of the Embodiment

In the above embodiment, when the humidity control system (10) is stopped, each heat exchanger chamber (37, 38) forms a closed space so that the discharge units (101, 102) generate active species in the respective heat exchanger chambers (37, 38) of the closed spaces. Thus, odorous components adsorbed by the adsorbent of each adsorption heat exchanger (51, 52) can be decomposed by the active species, whereby accumulation and concentration of the odorous components in the adsorbents can be prevented. This can prevent concentrated odorous components from being desorbed from the adsorbents and supplied into the room in the subsequent humidity control mode, making it possible to keep the room sufficiently comfortable.

Since each heat exchanger chamber (37, 38) forms a closed space, the concentration of the active species in each heat exchanger chamber (37, 38) can be increased. This can increase the efficiency of decomposition of the odorous components. Moreover, since each adsorption heat exchanger (51, 52) is located in a closed space, the remaining active species can also be prevented from leaking into the room and the like.

Moreover, the active species can prevent growth of bacteria and mold near the adhesion heat exchangers (51, 52). This enables clean air to be supplied into the room during the humidity control mode. This can also prevents reduction in desorption/adsorption capability of the adsorbent, which is caused by mold and the like growing on the surface of the adsorbent.

Since the dampers (41-48) for switching the air flow paths are used to form a closed space of each heat exchanger chamber (37, 38), no separate dampers need be provided additionally, whereby the number of parts can be minimized.

Moreover, in the above embodiment, the operation of discharging the air in each heat exchanger chamber (37, 38) out of the room is performed before the normal operation is resumed after the odor decomposition operation. This enables the active species remaining in the heat exchanger chambers (37, 38) to be reliably discharged out of the room, and thus, can reliably prevent the active species from being supplied into the room in the subsequent humidity control mode.

Other Embodiments

Although the streamer discharge apparatus is used as the active species generating unit in the above embodiment, other discharge apparatuses, such as those for generating, e.g., a corona discharge, a glow discharge, and the like may be used, or an ozone generator and the like may be used.

Although the discharge units (101, 102) are positioned on the outlet side of the respective adsorption heat exchangers (51, 52) in the above embodiment, the discharge units (101, 102) may be positioned on the inlet side of the respective adsorption heat exchangers (51, 52).

Note that the above embodiments are essentially preferable examples, and are not intended to limit the scope of the present invention, its applications, or its uses.

INDUSTRIAL APPLICABILITY

As described above, the present invention is useful for humidity control systems for controlling the humidity in a room by using an adsorbent for adsorbing and desorbing moisture.

The invention claimed is:

1. A humidity control system, comprising:
a casing having air passages formed therein;
two adsorption heat exchangers, which are provided in the air passages of the casing, and support thereon an adsorbent capable of adsorbing moisture in air and desorbing moisture into the air;
a compressor;
an air discharge fan;
an air supply fan;
a closed space forming unit for forming each of closed spaces located around each of the adsorption heat exchangers so as to hermetically seal each of the adsorption heat exchangers therein; and
an active species generating unit for supplying active species, for decomposing odorous components, into each of the closed spaces, wherein
a plurality of open/close dampers are provided in the casing, where the open/close dampers are capable of switching air flow paths by connecting and disconnecting the air passages, located on inlet and outlet sides of the adsorption heat exchangers, to and from each other,
the closed space forming unit is formed by the plurality of open/close dampers, where the open/close dampers form the closed spaces around each of the adsorption heat exchangers when closed,
the closed spaces are a first heat exchanger chamber and a second heat exchanger chamber,
when a command to stop the humidity control system is received from an operation section operated by an user, the compressor, the air discharge fan, and the air supply fan are stopped, and all of the open/close dampers located around the first heat exchanger chamber and the second heat exchanger chamber are closed, whereby each of the first heat exchanger chamber and the second heat exchanger chamber serves as a closed space, and
the active species generating unit supplies an active species to each of the closed spaces.

2. The humidity control system of claim 1, wherein
the humidity control system is configured to perform an operation of discharging air in one of the heat exchanger chambers out of the room, and air in another of the heat exchanger chambers out of the room at the same time.

3. The humidity control system of claim 1 or 2, wherein
the active species generating unit is formed by a streamer discharge apparatus for generating the active species by a streamer discharge.

\* \* \* \* \*